(12) United States Patent
Kimura et al.

(10) Patent No.: US 12,414,674 B2
(45) Date of Patent: Sep. 16, 2025

(54) IMAGE PROCESSING APPARATUS, DIAGNOSIS SUPPORTING METHOD, AND RECORDING MEDIUM RECORDING IMAGE PROCESSING PROGRAM

(71) Applicant: OLYMPUS CORPORATION, Tokyo (JP)

(72) Inventors: Mitsutaka Kimura, Hino (JP); Yamato Kanda, Hino (JP); Akihiro Kubota, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 1083 days.

(21) Appl. No.: 17/378,080

(22) Filed: Jul. 16, 2021

(65) Prior Publication Data

US 2021/0338042 A1    Nov. 4, 2021

Related U.S. Application Data

(63) Continuation of application No. PCT/JP2019/001712, filed on Jan. 21, 2019.

(51) Int. Cl.
*A61B 1/00* (2006.01)

(52) U.S. Cl.
CPC .... *A61B 1/00006* (2013.01); *A61B 1/000094* (2022.02); *A61B 1/00055* (2013.01)

(58) Field of Classification Search
CPC ............ A61B 1/00006; A61B 1/00094; A61B 1/00055; A61B 1/00002; A61B 90/361; A61B 1/000094
See application file for complete search history.

(56) References Cited

U.S. PATENT DOCUMENTS 6,483,485 B1 * 11/2002 Huang .................... G06F 3/011
                                                       348/E5.12
6,533,797 B1 *  3/2003 Stone ................. A61B 17/2909
                                                          606/1

(Continued)

FOREIGN PATENT DOCUMENTS

EP          1 862 106 A1    12/2007
JP         H02-166493 A      6/1990
(Continued)

OTHER PUBLICATIONS

Lee, A. et al., Endoscopist fatigue estimates and colonoscopic adenoma detection in a large community-based setting, Gastrointestinal Endoscopy, vol. 85, Issue 3 (Year: 2017).*

(Continued)

*Primary Examiner* — Alex M Valvis
*Assistant Examiner* — Jonathan M Haney
(74) *Attorney, Agent, or Firm* — Scully, Scott, Murphy & Presser, P.C.

(57) ABSTRACT

An image processing apparatus includes a processor. The processor receives an observation image of a subject or the observation image and system information, detects a lesioned part candidate from the observation image, estimates a deterioration risk of endoscopy quality from the observation image or the system information, controls a notification form of the lesioned part candidate from an estimation result of the deterioration risk, and notifies the lesioned part candidate according to the control of the notification form.

21 Claims, 18 Drawing Sheets

(56) References Cited

U.S. PATENT DOCUMENTS

| | | | |
|---|---|---|---|
| 2008/0119691 A1 | 5/2008 | Yagi et al. | |
| 2010/0228584 A1 | 9/2010 | Nash | |
| 2012/0262559 A1 | 10/2012 | On | |
| 2014/0275981 A1* | 9/2014 | Selover | A61B 5/061 600/424 |
| 2017/0164869 A1* | 6/2017 | Lee | A61B 34/20 |
| 2018/0325617 A1* | 11/2018 | Mezrich | A61B 90/30 |
| 2019/0254757 A1* | 8/2019 | Piron | A61B 5/7405 |

FOREIGN PATENT DOCUMENTS

| | | |
|---|---|---|
| JP | 2005-348936 A | 12/2005 |
| JP | 2006-255021 A | 9/2006 |
| JP | 2010-057727 A | 3/2010 |
| JP | 2010-262466 A | 11/2010 |
| JP | 2011-255006 A | 12/2011 |
| JP | 2012-217579 A | 11/2012 |
| JP | 2017-039364 A | 2/2017 |
| WO | 2006/100808 A1 | 9/2006 |

OTHER PUBLICATIONS

Harewood, G.C., et al. Impact of Operator Fatigue on Endoscopy Performance: Implications for Procedure Scheduling. Dig Dis Sci 54, 1656-1661. (Year: 2009).*

Mori, Y. et al., Novel computer-aided diagnostic system for colorectal lesions by using endocytoscopy (with videos), Gastrointestinal Endoscopy, vol. 81, Issue 3. (Year: 2015).*

Intentional Search report dated Mar. 19, 2019 received in PCT/JP2019/001712.

* cited by examiner

IMAGE PROCESSING APPARATUS, DIAGNOSIS SUPPORTING METHOD, AND RECORDING MEDIUM RECORDING IMAGE PROCESSING PROGRAM

CROSS REFERENCE TO RELATED APPLICATION

This application is a continuation application of PCT/JP2019/001712 filed on Jan. 21, 2019, the entire contents of which are incorporated herein by this reference.

BACKGROUND OF THE INVENTION

1. Field of the Invention

The present invention relates to an image processing apparatus, a diagnosis supporting method, and a recording medium recording an image processing program.

2. Description of the Related Art

Endoscopes have been widely used in a medical field and an industrial field. For example, in the medical field, a surgeon can find and identify a lesioned part by viewing an endoscopic image in a subject displayed on a display apparatus and perform treatment on the lesioned part using a treatment instrument.

There has been generally widely known an image processing apparatus that applies a marker such as a frame to and highlights a lesioned part detected from an endoscopic image in order to prevent a surgeon from overlooking the lesioned part when the surgeon views the endoscopic image.

In endoscopic observation, relative positions of an object in a body cavity, an image of which is picked up by an endoscope, and an insertion section of the endoscope inserted into the body cavity can always change. Therefore, it is difficult to correctly detect a once-detected lesioned part in all frames. Overlooking of a lesioned part candidate region easily occurs. Accordingly, Japanese Patent Application Laid-Open Publication No. 2006-255021 proposes a technique for temporally changing display intensity based on a display period in order to prevent the overlooking of the lesioned part candidate region. Japanese Patent Application Laid-Open Publication No. 2017-039364 discloses a technique for analyzing a sleepiness state of a user and changing a display method to reduce sleepiness (fatigue) to prevent a driving operation mistake of the user.

SUMMARY OF THE INVENTION

An image processing apparatus according to an aspect of the present invention includes a processor. The processor: receives an observation image of a subject or the observation image and system information; detects a lesioned part candidate from the observation image; estimates a deterioration risk of endoscopy quality from the observation image or the system information; controls a notification form of the lesioned part candidate from an estimation result of the deterioration risk; and notifies the lesioned part candidate according to the control of the notification form.

A non-transitory computer-readable recording medium recording an image processing program according to an aspect of the present invention records an image processing program for causing a computer to execute processing for: receiving an observation image of a subject or the observation image and system information; detecting a lesioned part candidate from the observation image; estimating a deterioration risk of endoscopy quality from the observation image or the system information; controlling a notification form of the lesioned part candidate from an estimation result of the deterioration risk of the endoscopy quality; and notifying the lesioned part candidate according to the control of the notification form.

A diagnosis supporting method according to an aspect of the present invention includes: detecting a lesioned part candidate from an observation image of a subject; estimating a deterioration risk of endoscopy quality from the observation image or system information; and notifying the lesioned part candidate in a notification form corresponding to an estimation result of the deterioration risk of the endoscopy quality.

DETAILED DESCRIPTION OF THE PREFERRED EMBODIMENTS

Embodiments of the present invention are explained in detail below with reference to the drawings.

First Embodiment

Figure 1:
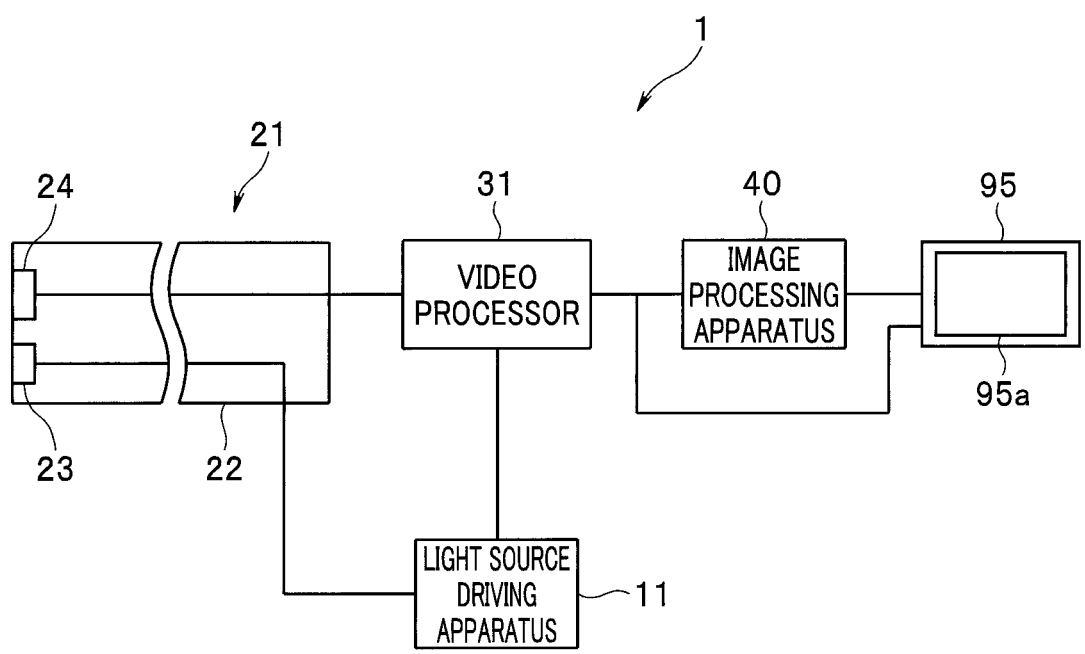
FIG. 1 is a diagram showing a configuration of a main part of an endoscope system including an endoscope apparatus according to a first embodiment.

FIG. 1 is a diagram showing a configuration of a main part of an endoscope system including an endoscope apparatus according to a first embodiment. The present embodiment is an embodiment for analyzing a history, an endoscopy state, and the like of a user to determine a state (a risk) in which endoscopy quality is likely to be deteriorated, and changing a display method according to the determination in order to prevent deterioration in the endoscopy quality. Consequently, in the present embodiment, for example, it is possible to prevent overlooking of a lesioned part candidate of the user. There is an effect of improving the endoscopy quality.

As shown in FIG. 1, an endoscope system 1 includes a light source driving apparatus 11, an endoscope 21, a video processor 31, an image processing apparatus 40, and a display apparatus 95.

The light source driving apparatus 11 includes, for example, a drive circuit. The light source driving apparatus 11 is connected to the endoscope 21 and the video processor 31. The light source driving apparatus 11 is configured to generate, based on a light source control signal from the video processor 31, a light source driving signal for driving a light source unit 23 of the endoscope 21 and output the generated light source driving signal to the endoscope 21.

The endoscope 21 is connected to the light source driving apparatus 11 and the video processor 31. The endoscope 21 includes an insertion section 22 having an elongated shape insertable into a body cavity of an examinee. The light source unit 23 and an image pickup unit 24 are provided at a distal end portion of the insertion section 22.

The light source unit 23 includes a light emitting element such as a white LED. The light source unit 23 is configured to emit light according to a light source driving signal outputted from the light source driving apparatus 11 to generate illumination light and emit the generated illumination light to an object such as biological tissue.

The image pickup unit 24 includes an image sensor such as a color CCD or a color CMOS. The image pickup unit 24 is configured to perform operation corresponding to an image pickup control signal outputted from the video processor 31. The image pickup unit 24 is configured to receive reflected light from an object illuminated by the illumination light emitted from the light source unit 23, pick up an image of the received reflected light and generate an image pickup signal, and output the generated image pickup signal to the video processor 31.

The video processor 31 is connected to the light source driving apparatus 11 and the endoscope 21. The video processor 31 is configured to generate alight source control signal for controlling a light emission state of the light source unit 23 and output the light source control signal to the light source driving apparatus 11. The video processor 31 is configured to generate and output an image pickup control signal for controlling an image pickup operation of the image pickup unit 24. The video processor 31 applies predetermined processing to the image pickup signal outputted from the endoscope 21 to generate an observation image of the object. The video processor 31 is configured to apply highlighting processing and white balance correction processing to the generated observation image and, subsequently, sequentially output the observation image to the image processing apparatus 40 frame by frame and output the generated observation image to the display apparatus 95 as an image for display.

The image processing apparatus 40 includes an electronic circuit such as an image processing circuit. The image processing apparatus 40 is configured to generate an image for display based on the observation image outputted from the video processor 31 and perform operation for causing the display apparatus 95 to display the generated image for display.

The display apparatus 95 includes a monitor or the like and is configured to be able to display the observation image from the video processor 31 and to display the image for display outputted from the image processing apparatus 40.

Figure 2:
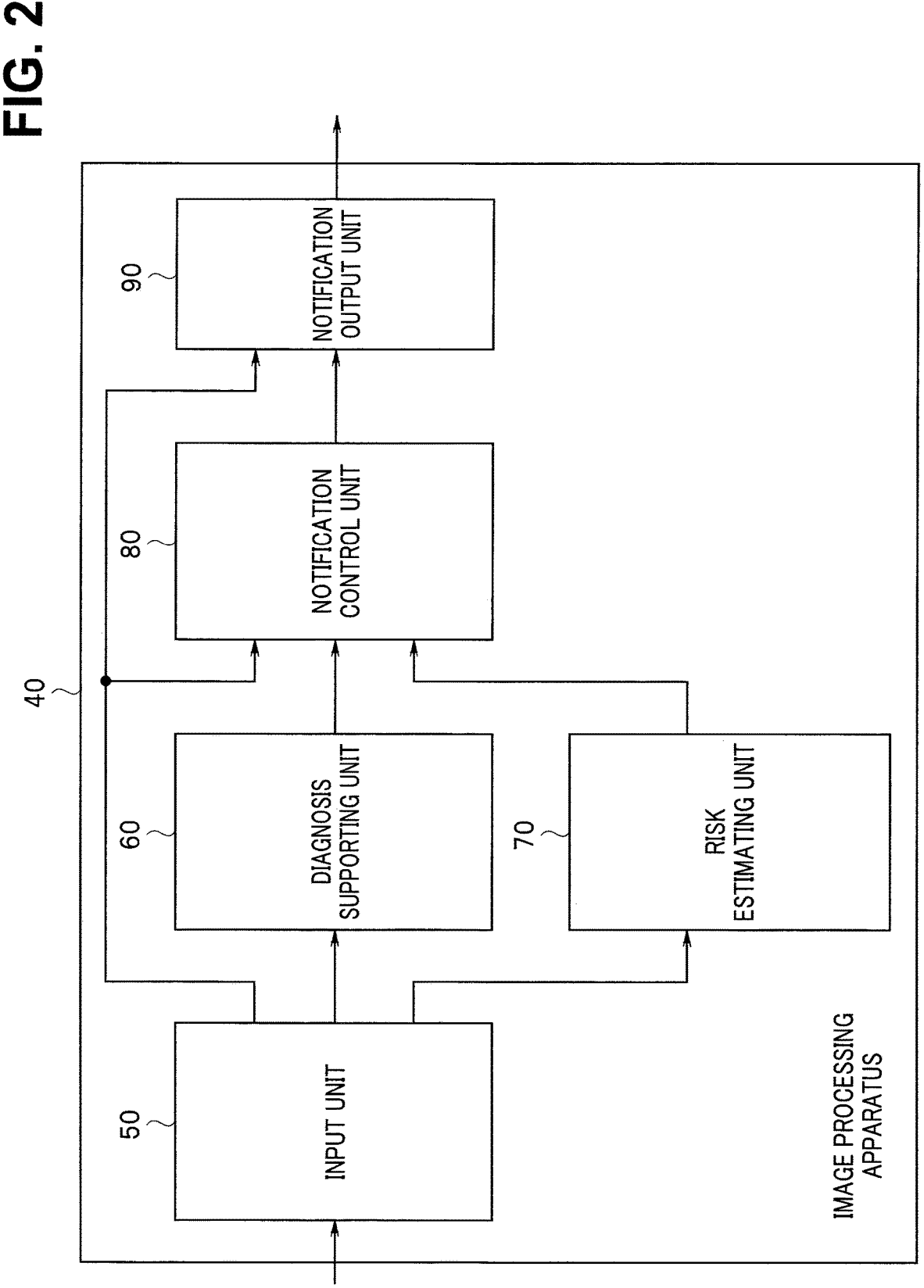
FIG. 2 is a block diagram showing an example of a specific configuration of an image processing apparatus 40 in FIG. 1.

FIG. 2 is a block diagram showing an example of a specific configuration of the image processing apparatus 40 in FIG. 1.

As shown in FIG. 2, the image processing apparatus 40 includes an input unit 50, a diagnosis supporting unit 60, a risk estimating unit 70, a notification control unit 80, and a notification output unit 90. Note that the diagnosis supporting unit 60, the risk estimating unit 70, and the notification control unit 80 may be configured by a processor using a CPU or an FPGA, may operate according to a program stored in a not-shown memory to control the respective units, or may realize a part or all of functions with a hardware electronic circuit.

The input unit 50 captures the observation image inputted from the video processor 31 and outputs the observation image to the diagnosis supporting unit 60. The input unit 50 may be configured to capture system information from the video processor 31. Note that the system information is included in header information of the observation image and inputted in some cases and is inputted as data separate from the observation image in other cases. In the present embodiment, the system information includes a history and an endoscopy state of the user. The input unit 50 outputs the inputted observation image to the diagnosis supporting unit 60 and the risk estimating unit 70. The input unit 50 is configured to, when the system information is inputted separately from the observation image, output the inputted system information to the risk estimating unit 70.

The diagnosis supporting unit 60 is configured to detect, with a publicly-known method, a lesioned part candidate based on the inputted observation image. The diagnosis supporting unit 60 outputs information concerning the detected lesioned part candidate to the notification control unit 80.

The notification control unit 80 receives the observation image from the input unit 50, receives the information concerning the lesioned part candidate from the diagnosis supporting unit 60, and generates, in the observation image, information for notifying a detection result of the lesioned part candidate detected by the diagnosis supporting unit 60. The notification control unit 80 outputs the generated information to the notification output unit 90. The notification output unit 90 is configured to notify the detection result of the lesioned part candidate to the user based on the information outputted from the notification control unit 80. For example, the notification output unit 90 notifies the detection result of the lesioned part candidate to the user with notification by an image, notification by sound, or the like.

For example, when the notification output unit 90 performs the notification by an image, the notification control unit 80 generates information for displaying an image indicating a position of the lesioned part candidate (hereinafter referred to as detection marker) on the observation image and outputs the information to the notification output unit 90. The notification output unit 90 generates an image for display obtained by combining, with the observation image received from the input unit 50, the image of the detection marker based on the information outputted from the notification control unit 80. The notification output unit 90 gives the generated image for display to the display apparatus 95 and displays the image for display on a display screen 95*a*.

In this case, the doctor or the like performs final determination with the observation image and the detection marker displayed on the display screen 95*a* of the display apparatus 95 referring to the lesioned part candidate detected by the diagnosis supporting unit 60. In this case, it is likely that the detection marker is overlooked or attentiveness is reduced according to experience, a fatigue degree, or the like of the doctor or the like who observes the observation image. Note that the same problem occurs when the notification is performed by sound. For example, depending on magnitude of volume and a notification period, there are problems in that a hearing error occurs and attentiveness is reduced by the sound.

Accordingly, in the present embodiment, the risk estimating unit 70 is provided in order to optimize a notification form of the notification by the notification control unit 80 according to the user. The risk estimating unit 70 is configured to estimate, based on the observation image, a risk of deterioration in endoscopy quality and output an estimation result of the risk to the notification control unit 80. Note that the risk estimating unit 70 may be configured to estimate the risk of deterioration in the endoscopy quality using the system information. In other words, the risk estimating unit 70 estimates a risk based on at least one of the observation image or the system information.

For example, the risk estimating unit 70 may use, based on the observation image and the system information, an analysis result of a fatigue degree and an experience level of the user as an estimation result of the risk of deterioration in the endoscopy quality. The risk estimating unit 70 generates a risk estimation result for changing the notification form to prevent overlooking.

For example, when the notification is performed by the image, the risk estimating unit 70 estimates the risk of deterioration in the endoscopy quality in order to perform change control for a display form of the detection marker. The notification control unit 80 optimizes, following the risk estimation result, the display form of the detection marker according to the user. Note that, in the following explanation, an example in which the notification is performed using the image is explained. However, the same control is possible when the notification is performed by sound.

The notification control unit 80 is configured to receive the risk estimation result of the risk estimating unit 70 and change the display form of the detection marker. The notification control unit 80 can cause the user to recognize presence or absence of detection of a lesioned part candidate according to display or non-display of the detection marker and cause the user to recognize a position of a lesioned part in a body according to a display position in the observation image. In this way, the detection marker is displayed in, for example, a display form corresponding to the risk estimation result, which is the analysis result of the fatigue degree and the experience level of the user. It is possible to prevent overlooking and improve endoscopy quality.

Figure 3:
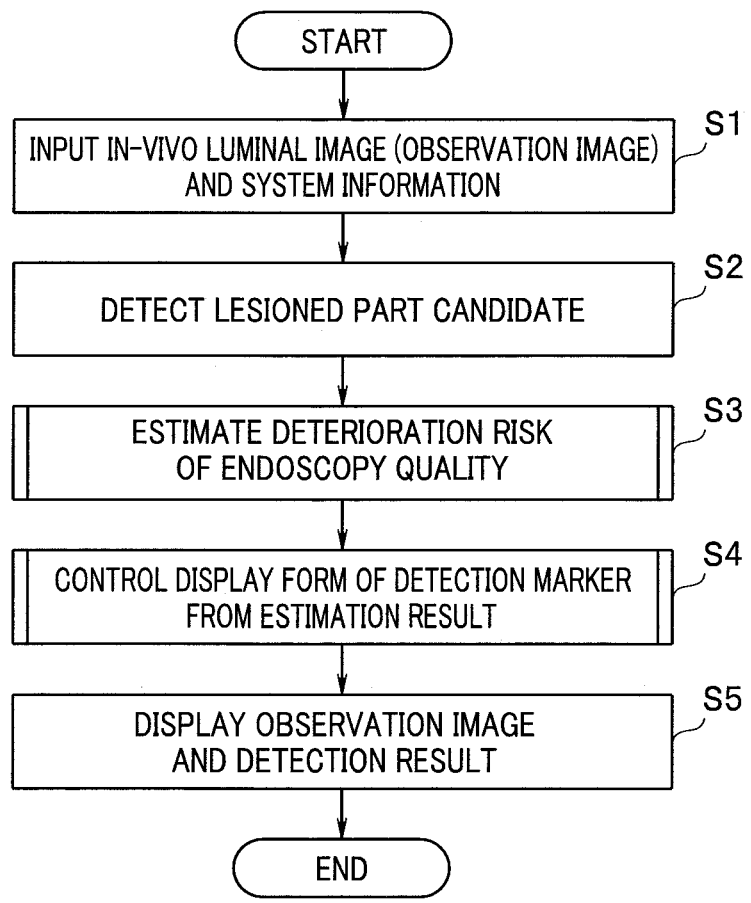
FIG. 3 is a flowchart for explaining the first embodiment.

Subsequently, operation in the embodiment configured as explained above is explained with reference to FIG. 3. FIG. 3 is a flowchart for explaining the first embodiment.

For example, when the light source driving apparatus 11 and the video processor 31 are turned on, the endoscope 21 emits illumination light to an object, receives reflected light from the object, picks up an image of the received reflected light and generates an image pickup signal, and outputs the generated image pickup signal to the video processor 31.

The video processor 31 applies predetermined processing to the image pickup signal outputted from the endoscope 21 to generate an observation image of the object and sequentially outputs the generated observation image to the image processing apparatus 40 frame by frame. In other words, the input unit 50 acquires an endoscopic image (the observation image), which is an in-vivo luminal image, from the video processor 31 (S1). The system information may be included in header information of the observation image. The input unit 50 may be configured to, when the system information is not included in the header information of the observation image, capture the system information separately from the observation image. Note that the input unit 50 may be configured to capture only the observation image not including the system information.

Subsequently, in step S2, the diagnosis supporting unit 60 receives the observation image from the input unit 50, detects a lesioned part candidate from the observation image, and outputs a detection result to the notification control unit 80.

In step S3, the risk estimating unit 70 receives at least one of the observation image or the system information from the input unit 50 and estimates a risk of deterioration in endoscopy quality. The risk estimating unit 70 outputs an estimation result of the risk to the notification control unit 80. Note that steps S2 and S3 may be execute in order of steps S3 and S2 or may be simultaneously executed.

The notification control unit 80 generates information for displaying, on the observation image received from the input unit 50, a detection marker for specifying the lesioned part candidate detected by the diagnosis supporting unit 60. In the present embodiment, the notification control unit 80 generates information for displaying a detection marker in a display form corresponding to the estimation result of the risk by the risk estimating unit 70 (S4).

The notification output unit 90 displays the detection marker on the display screen 95*a* of the display apparatus 95 based on the information outputted from the notification control unit 80 (S5). Note that an image obtained by superimposing the detection marker on the observation image may be outputted from the notification output unit 90, or that the image of the detection marker may be outputted from the notification output unit 90 and the display apparatus 95 may display the detection marker in a manner superimposed on the observation image from the video processor 31.

As explained above, in the present embodiment, the risk of deterioration in the endoscopy quality is estimated and the display method is changed according to a result of the estimation in order to prevent the deterioration in the endoscopy quality. Consequently, it is possible to improve the endoscopy quality.

Second Embodiment

Figure 4:
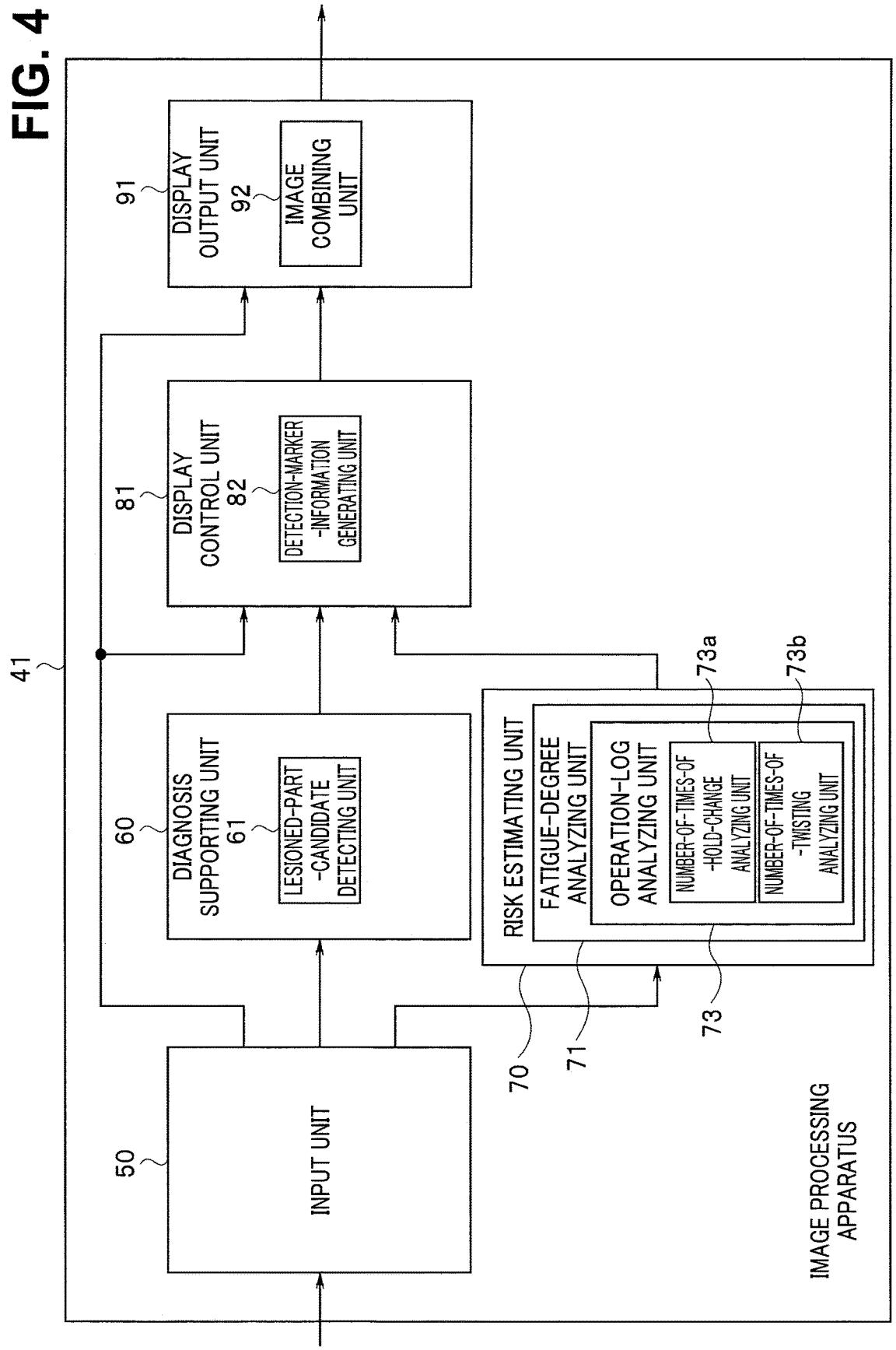
FIG. 4 is a block diagram showing a second embodiment of the present invention.

FIG. 4 is a block diagram showing a second embodiment of the present invention. An endoscope system in the present embodiment is different from the endoscope system 1 shown in FIG. 1 in that an image processing apparatus 41 is adopted instead of the image processing apparatus 40. FIG. 4 shows an example of a specific configuration of the image processing apparatus 41. The present embodiment is an example in which a risk of deterioration in endoscopy quality is estimated according to an analysis of a fatigue degree of a user.

A configuration of the input unit 50 in FIG. 4 is the same as the configuration shown in FIG. 2. In the present embodiment, the example is explained in which a display control unit 81 is adopted as a specific example of the notification control unit 80 and a display output unit 91 is adopted as a specific example of the notification output unit 90.

The input unit 50 outputs an observation image to the diagnosis supporting unit 60 and the display control unit 81. The input unit 50 outputs at least one of the observation image or the system information to the risk estimating unit 70. The display output unit 91 displays an image for display outputted from the display control unit 81 on the display screen 95a of the display apparatus 95.

In the present embodiment, the diagnosis supporting unit 60 includes a lesioned-part-candidate detecting unit 61. The lesioned-part-candidate detecting unit 61 is configured to detect a lesioned part candidate included in the observation image sequentially outputted from the input unit 50. The lesioned-part-candidate detecting unit 61 detects a lesioned part candidate from the observation image by performing processing for applying, to the observation image, an image discriminator that acquires, in advance, with a learning method such as deep learning, a function capable of discriminating a lesioned part candidate. Note that the detection of the lesioned part candidate is not limited to the learning method described above and other methods may be used. For example, polyp candidate detection processing disclosed in Japanese Patent Application Laid-Open Publication No. 2007-244518 may be used.

The lesioned-part-candidate detecting unit 61 is configured to determine a region on the observation image of the detected lesioned part candidate (hereinafter referred to as lesioned part candidate region) and output information indicating the lesioned part candidate region to the display control unit 81 as a detection result of the lesioned part candidate.

The display control unit 81 includes a detection-marker-information generating unit 82. The detection-marker-information generating unit 82 receives the information indicating the lesioned part candidate region and, in order to cause the user to recognize presence of the lesioned part candidate detected in the diagnosis supporting unit 60, generates, for example, information for generating an image (a detection marker) surrounding the lesioned part candidate region in the observation image and outputs the information to the display output unit 91.

The display output unit 91 includes an image combining unit 92. The image combining unit 92 generates, based on the information outputted from the display control unit 81, an image for display obtained by superimposing the detection marker in the observation image received from the input unit 50 and outputs the image for display to the display apparatus 95. Note that the display output unit 91 is also configured to be able to output the detection marker from the detection-marker-information generating unit 82 as-is without combining the detection marker with the observation image. The display apparatus 95 may also be configured to display the detection marker from the display output unit 91 in a manner superimposed in the observation image from the video processor 31.

The detection marker generated by the information of the detection-marker-information generating unit 82 has a form necessary for enabling the user to visually recognize presence of the lesioned part candidate. For example, a shape of the detection marker may be a quadrangle, a triangle, a circle, a star shape, or the like or may be any other shapes in some cases. The detection marker may be an image not surrounding the lesioned part candidate if the detection marker can indicate the presence and a position of the lesioned part candidate. Further, the detection-marker-information generating unit 82 may generate a message indicating a lesioned part as support information and display the message in a form of a popup message or the like near the lesioned part to indicate the presence of the lesioned part.

In the present embodiment, the detection-marker-information generating unit 82 is configured to change the display form of the detection marker based on the risk estimation result of the risk estimating unit 70. In other words, the detection-marker-information generating unit 82 changes the display form to cause the user to easily recognize the presence of the lesioned part candidate and prevent the observation image from being confirmed as much as possible. In this case, in the present embodiment, the risk estimating unit 70 is configured to control, following the risk estimation result based on an analysis of a fatigue degree of the user, the change of the display form by the detection-marker-information generating unit 82.

The risk estimating unit 70 includes a fatigue-degree analyzing unit 71. The fatigue-degree analyzing unit 71 analyzes the fatigue degree of the user to obtain an analysis result. The risk estimating unit 70 may use an analysis result of the fatigue-degree analyzing unit 71 as a risk estimation result. In the present embodiment, the fatigue-degree analyzing unit 71 is configured by an operation-log analyzing unit 73. The operation-log analyzing unit 73 analyzes an operation log of the endoscope 21 to analyze the fatigue degree of the user. In the present embodiment, as an example, the operation-log analyzing unit 73 is configured by a number-of-times-of-hold-change analyzing unit 73a and a number-of-times-of-twisting analyzing unit 73b.

The number-of-times-of-hold-change analyzing unit 73a is configured to analyze, with the operation log of the endoscope 21, the number of times of hold change of the endoscope 21. For example, the number-of-times-of-hold-change analyzing unit 73a calculates the number of times the user changes the hold of the insertion section 22 of the endoscope 21 in any period acquired by a predetermined method. In an act of the user changing the hold of the insertion section 22, a hand of the user is removed from the insertion section 22. Therefore, the act appears as a change such as shaking of the observation image. For example, the number-of-times-of-hold-change analyzing unit 73a may detect such a change of the observation image with an image analysis for the observation image to analyze the change of the hold of the insertion section 22 by the user and acquire the number of times of the hold change. For example, it is also possible to attach a not-shown acceleration sensor or the like to the insertion section 22 in order to analyze the number of times of hold change by analyzing an output of the acceleration sensor. The risk estimating unit 70 may acquire such an output of the acceleration sensor as the system information to analyze the number of times of hold change.

Note that information in a period including the any period can be acquired by various methods. The image processing apparatus 40 and respective image processing apparatuses explained below may acquire a set period from a not-shown device such as a timer or a sensor, may acquire the set period from information concerning a photographing time included in image information, or may acquire the set period from system information based on user setting.

The number-of-times-of-twisting analyzing unit 73b is configured to analyze, with the operation log of the endoscope 21, the number of times of twisting of the endoscope 21. For example, the number-of-times-of-twisting analyzing unit 73b includes a not-shown timer and calculates the number of times the user twists the insertion section 22 of the endoscope 21 in any period. In an act of the user twisting the insertion section 22, the insertion section 22 rotates. Therefore, the act appears as a change in which the observation image rotates. For example, the number-of-times-of-twisting analyzing unit 73b may detect such a change of the observation image with an image analysis for the observation image to analyze the twisting of the insertion section 22 by the user and acquire the number of times of the twisting. For example, it is also possible to attach a not-shown gyro sensor or the like to the insertion section 22 in order to analyze the number of times of twisting by analyzing an output of the gyro sensor. The risk estimating unit 70 may analyze the number of times of twisting by acquiring such an output of the gyro sensor as the system information.

The fatigue-degree analyzing unit 71 may analyze the fatigue degree of the user according to at least one of the number of times of hold change calculated by the number-of-times-of-hold-change analyzing unit 73a or the number of times of twisting calculated by the number-of-times-of-twisting analyzing unit 73b and set an analysis result as the risk estimation result. For example, the fatigue-degree analyzing unit 71 may determine that the fatigue degree is higher as the number of times of hold change or the number of times of twisting of the endoscope 21 by the user is larger and estimate that the risk of deterioration in the endoscopy quality increases. Conversely, the risk estimating unit 70 may determine that the fatigue degree is lower as the number of times of hold change or the number of times of twisting of the endoscope 21 by the user is smaller and estimate that the risk of deterioration in the endoscopy quality decreases. The risk estimation result based on the fatigue degree of the user outputted from the risk estimating unit 70 is supplied to the display control unit 81.

Note that, in the present embodiment, the example is explained in which the operation-log analyzing unit 73 is configured by the number-of-times-of-hold-change analyzing unit 73a and the number-of-times-of-twisting analyzing unit 73b. However, the operation-log analyzing unit 73 may be configured by one of the number-of-times-of-hold-change analyzing unit 73a and the number-of-times-of-twisting analyzing unit 73b.

Figure 5:
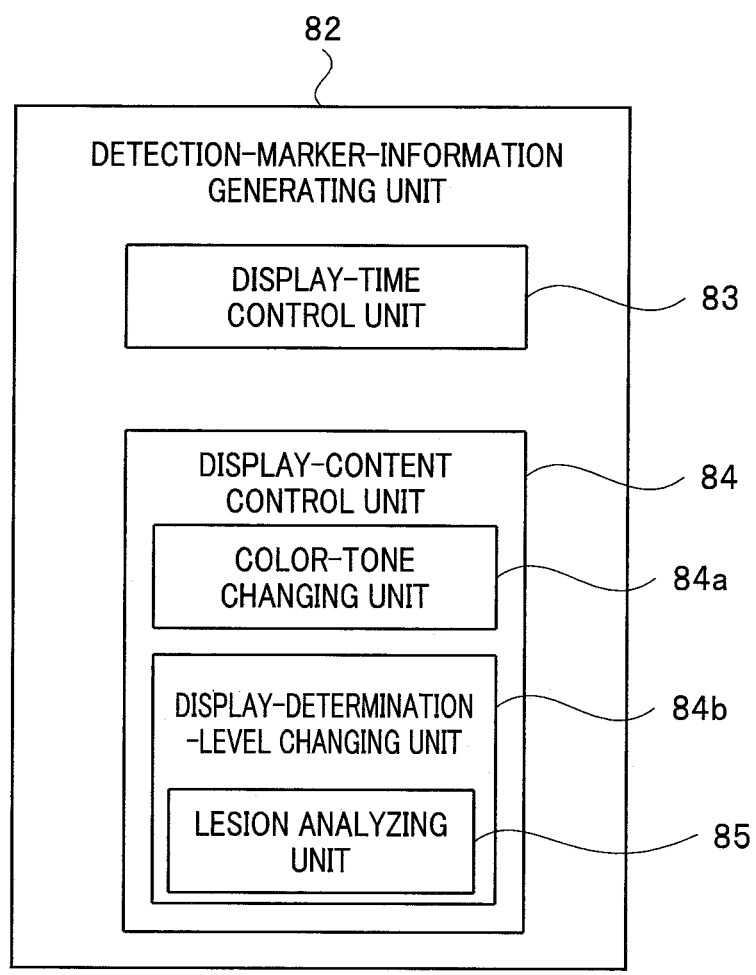
FIG. 5 is a block diagram showing an example of a specific configuration of a detection-marker-information generating unit 82.

FIG. 5 is a block diagram showing an example of a specific configuration of the detection-marker-information generating unit 82.

In FIG. 5, an example is shown in which the detection-marker-information generating unit 82 is configured by a display-time control unit 83 and a display-content control unit 84. The display-time control unit 83 changes a display time of the detection marker based on the inputted risk estimation result. For example, the display-time control unit 83 may set a display time corresponding to the fatigue degree of the user indicated by the risk estimation result. For example, the display time can be set longer as the fatigue degree of the user is higher and can be set shorter as the fatigue degree of the user is lower.

The display-content control unit 84 changes content (quality) of the display of the detection marker based on the inputted risk estimation result. In the example shown in FIG. 5, the display-content control unit 84 is configured by a color-tone changing unit 84a and a display-determination-level changing unit 84b. The color-tone changing unit 84a changes a color tone of the detection marker based on the inputted risk estimation result. For example, the color-tone changing unit 84a may set a color tone corresponding to the fatigue degree of the user indicated by the risk estimation result. For example, the color-tone changing unit 84a may set the detection marker to a more conspicuous color tone as the fatigue degree of the user is higher. For example, the color-tone changing unit 84a may set brightness and chroma of the detection marker higher as the fatigue degree of the user is higher. In this case, the detection marker is sensuously more conspicuous display as the fatigue degree of the user is higher. Conversely, the detection marker can sensuously have a more natural color as the fatigue degree of the user is lower.

The display-determination-level changing unit 84b changes a determination level of display and non-display (hereinafter referred to as display determination level) of the detection marker based on the inputted risk estimation result. Note that the detection marker is explained as being less easily displayed as the display determination level is lower and being more easily displayed as the display determination level is higher. For example, even if the lesioned part candidate is the same, the detection marker sometimes is not displayed if the display determination level is low and is sometimes displayed if the display determination level is high.

The display-determination-level changing unit 84b may determine the display determination level based on only the risk estimation result. However, in the example shown in FIG. 5, the display-determination-level changing unit 84b includes a lesion analyzing unit 85 in order to determine the display determination level. The lesion analyzing unit 85 is configured to analyze a nature of the lesioned part candidate detected by the lesioned-part-candidate detecting unit 61. The lesion analyzing unit 85 analyzes whether the lesioned part candidate is easily overlooked. For example, the lesion analyzing unit 85 receives information such as a shape, a size, and a color of the lesioned part candidate from the lesioned-part-candidate detecting unit 61 and determines a degree of overlooking likelihood.

The display-determination-level changing unit 84b determines the display determination level based on the fatigue degree of the user indicated by the risk estimation result and the degree of overlooking likelihood. The display determination level is set to a higher value as the degree of overlooking likelihood is higher. The display-determination-level changing unit 84b is configured to set the display determination level to a higher value as the fatigue degree of the user is higher. Therefore, with the control by the display-determination-level changing unit 84b, the detection marker is more easily displayed as the lesioned part candidate is more easily overlooked and the fatigue degree is higher and the detection marker is less easily displayed as the lesioned part candidate is less easily overlooked and the fatigue degree is lower.

Subsequently, operation in the embodiment configured as explained above is explained with reference to FIG. 6 to FIG. 10. FIG. 6 to FIG. 9 are flowcharts for explaining operation in the second embodiment. FIG. 10 is an explanatory diagram for explaining display examples.

The operation in the present embodiment is the same as the operation shown in FIG. 3. The present embodiment explains an example of a specific flow about steps S3 and S4 in FIG. 3.

When the light source driving apparatus 11 and the video processor 31 are turned on, the endoscope 21 emits illumination light to an object, receives reflected light from the object, picks up an image of the received reflected light and generates an image pickup signal, and outputs the generated image pickup signal to the video processor 31.

The video processor 31 applies predetermined processing to the image pickup signal outputted from the endoscope 21 to generate an observation image of the object and sequentially outputs the generated observation image to the image processing apparatus 41 frame by frame. The input unit 50 acquires an endoscopic image (the observation image), which is an in-vivo luminal image, from the video processor 31 (S1 in FIG. 3). Note that system information is sometimes included in the observation image. The input unit 50 outputs the acquired image to the diagnosis supporting unit 60 and the risk estimating unit 70. Note that when the system information is inputted separately from the observation image, the input unit 50 outputs the acquired system information to the risk estimating unit 70.

The lesioned-part-candidate detecting unit 61 detects a lesioned part candidate from the observation image using a learning method such as deep learning (S2 in FIG. 3). The lesioned-part-candidate detecting unit 61 determines a lesioned part candidate region indicating a range in an image of the detected lesioned part candidate and outputs information indicating the lesioned part candidate region to the display control unit 81 as a detection result of the lesioned part candidate.

Figure 6:
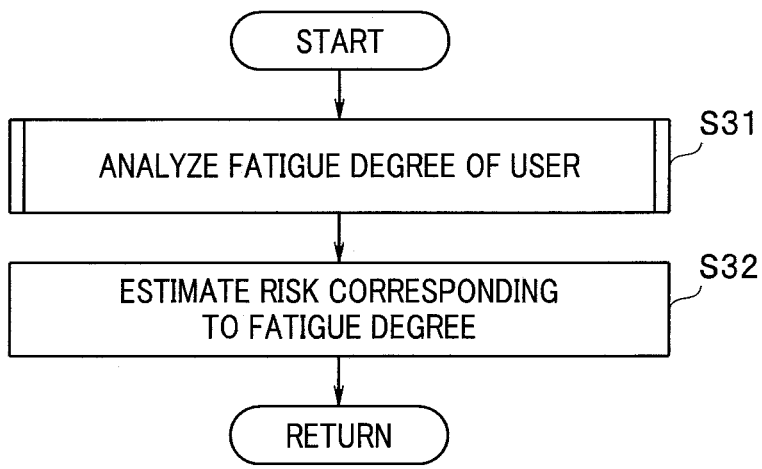
FIG. 6 is a flowchart for explaining operation in a second embodiment.
Figure 7:
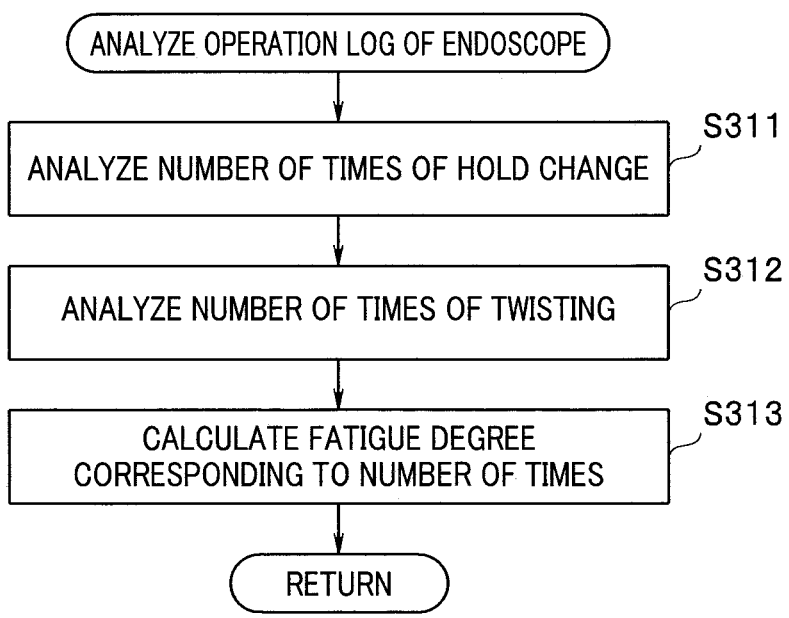
FIG. 7 is a flowchart for explaining the operation in the second embodiment.

On the other hand, the fatigue-degree analyzing unit 71 of the risk estimating unit 70 analyzes a fatigue degree of the user in step S31 in FIG. 6. For example, the fatigue-degree analyzing unit 71 analyzes an operation log of the endoscope 21 with the operation-log analyzing unit 73. FIG. 7 shows a specific flow of the operation-log analyzing unit 73. The operation-log analyzing unit 73 analyzes the number of times of hold change of the endoscope 21 with the number-of-times-of-hold-change analyzing unit 73a (S311). The operation-log analyzing unit 73 analyzes the number of times of twisting of the endoscope 21 with the number-of-times-of-twisting analyzing unit 73b (S312).

Note that the analysis of the number of times of hold change and the analysis of the number of times of twisting in steps S311 and S312 may be performed in reverse order or only one of the analyses may be performed. The fatigue-degree analyzing unit 71 calculates a fatigue degree based on an analysis result of at least one of the analyzed number of times of hold change or the analyzed number of times of twisting (S313). The fatigue-degree analyzing unit 71 outputs the calculated fatigue degree to the display control unit 81 as a risk estimation result. Note that the fatigue-degree analyzing unit 71 may set the analyzed number of times as an analysis result of the fatigue degree and directly output the analysis result of the fatigue degree as the risk estimation result. In this case, it is estimated that the fatigue degree is higher and a risk of deterioration in quality is higher as the analyzed number of times is larger.

The detection-marker-information generating unit 82 of the display control unit 81 sets a form of the detection marker based on the inputted risk estimation result and generates information for displaying the detection marker corresponding to the setting. For example, the detection-marker-information generating unit 82 sets, with the display-time control unit 83, a display time based on the risk estimation result (S41 in FIG. 8). The detection-marker-information generating unit 82 sets, with the display-content control unit 84, display content based on the risk estimation result (S42 in FIG. 8). Note that the settings in step S41 and S42 may be performed in reverse order or only one of the settings may be performed.

Figure 8:
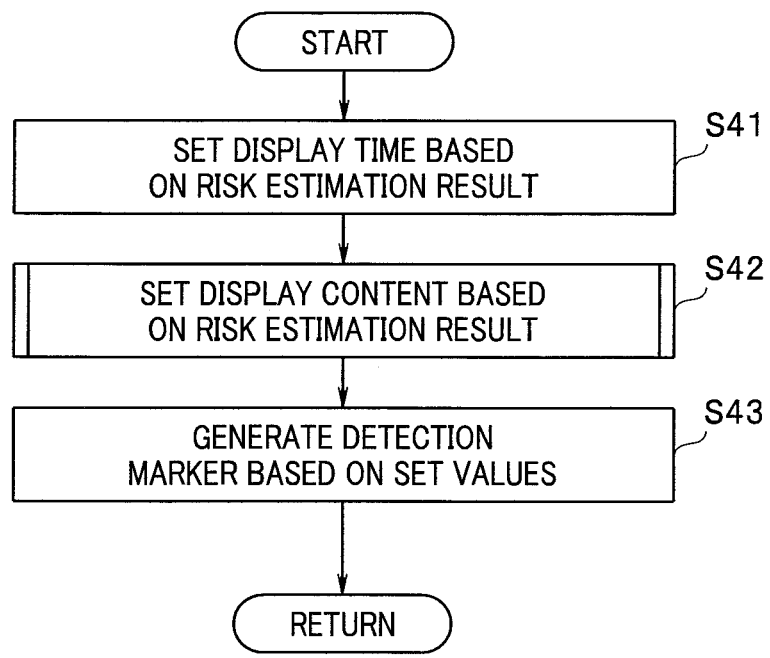
FIG. 8 is a flowchart for explaining the operation in the second embodiment.
Figure 9:
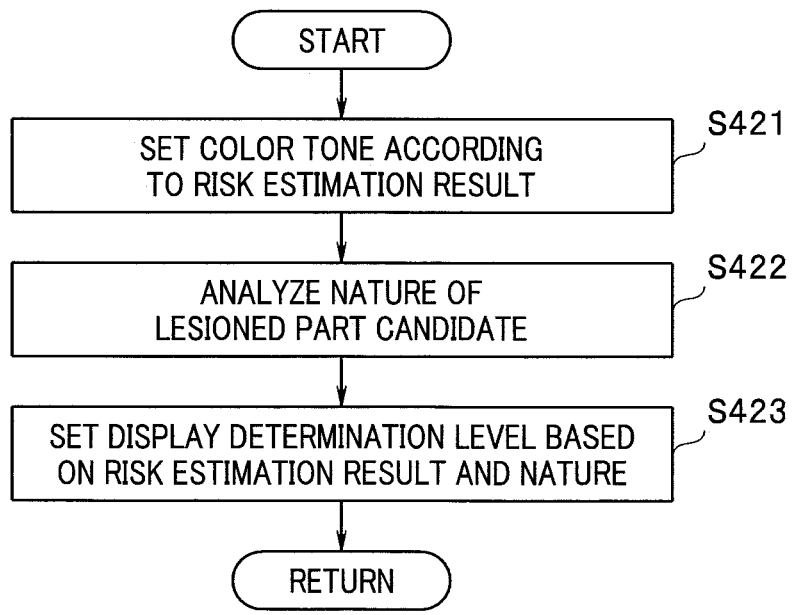
FIG. 9 is a flowchart for explaining the operation in the second embodiment.
Figure 10:
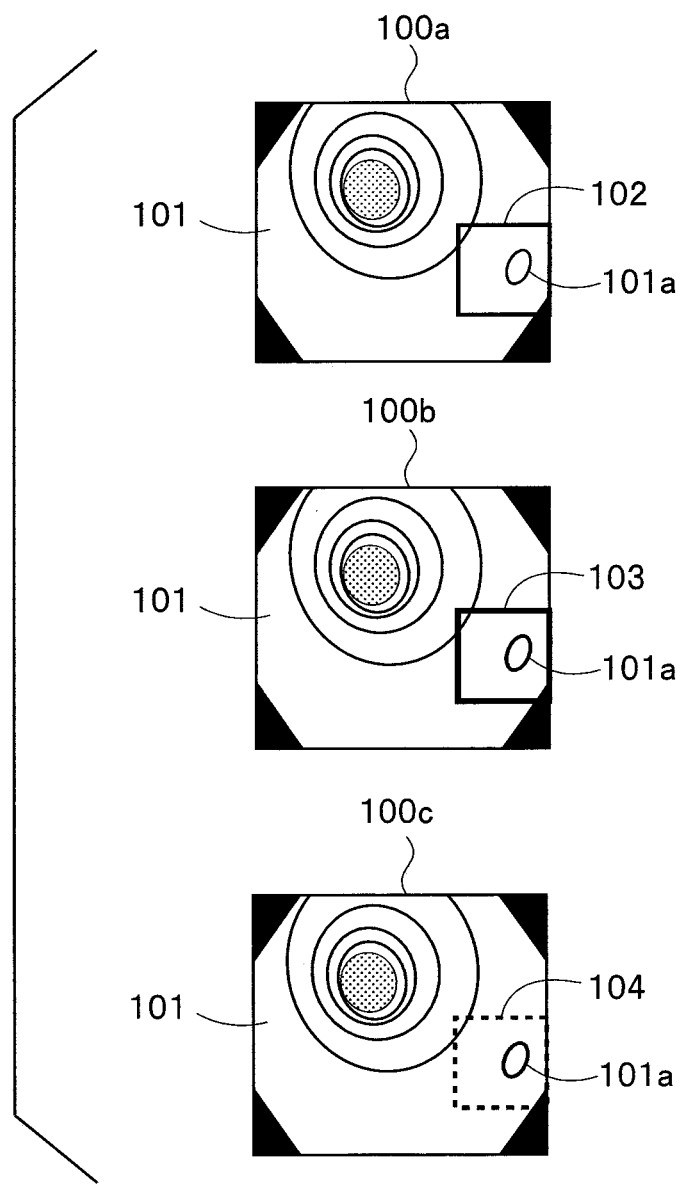
FIG. 10 is an explanatory diagram for explaining display examples.

FIG. 9 shows an example of a specific flow of step S42 in FIG. 8. For example, the display-content control unit 84 changes, with the color-tone changing unit 84a, a color tone according to the risk estimation result (S421 in FIG. 9). For example, when the risk estimation result indicates that the risk of deterioration in the endoscopy quality is relatively high, the color-tone changing unit 84a sets the detection marker to a conspicuous color tone.

The display-content control unit 84 determines a display determination level with the display-determination-level changing unit 84b. For example, in step S422, the display-determination-level changing unit 84b analyzes a nature of the lesioned part candidate. The display-determination-level changing unit 84b determines the display determination level based on the risk estimation result and the nature of the lesioned part candidate (S423). For example, about a lesioned part candidate having a small size and an easily overlooked nature, the display-determination-level changing unit 84b sets the display determination level high to make it easy to display the lesioned part candidate. The display-determination-level changing unit 84b further changes the display determination level according to the risk estimation result. For example, when the fatigue degree of the user is relatively high, the display-determination-level changing unit 84b sets the display determination level higher to make it easy to display the lesioned part candidate.

Note that the settings in step S421 and step S423 may be performed in reverse order or only the setting in step S421 may be performed. The display-determination-level changing unit 84b may change a predetermined display determination level according to only the risk estimation result to determine the display determination level.

In step S43, the detection-marker-information generating unit 82 generates, based on the setting of at least one of the set display time, the set color tone, or the set display determination level, information for displaying the detection marker and outputs the information to the display output unit 91. The image combining unit 92 of the display output unit 91 generates, based on the information outputted from the detection-marker-information generating unit 82, an image for display obtained by superimposing the detection marker on the observation image and gives the image for display to the display apparatus 95. Consequently, the display apparatus 95 displays the observation image superimposed with the detection marker on the display screen 95a.

FIG. 10 shows examples of images displayed on the display screen 95a of the display apparatus 95. Images 101a to 101c shown in FIG. 10 indicate, with respect to the same observation image 101, three display examples of detection markers in the cases in which risk estimation results are different. In the observation image 101, a lesioned part candidate 101a detected by the diagnosis supporting unit 60 is present. Detection markers 102 to 104 are displayed to surround the lesioned part candidate 101a.

For example, the detection marker 102 is a display example in the case of a medium fatigue degree. The detection marker 103 is a display example in the case of a large fatigue degree. The detection marker 104 is a display example in the case of an extremely small fatigue degree. On the figure, the detection marker 103 is displayed by a thicker line compared with the detection marker 102 to indicate that, for example, the detection marker 103 is a display corresponding to a relatively high display determination level in a relatively long display time and a relatively conspicuous color tone.

As an example of the change of the display content, the color tone and the display determination level are explained. However, as shown in FIG. 10, thickness of a line of a frame of a detection marker, a type of the frame, and the like may be changed. For example, the thickness of the line of the frame of the detection marker may be increased as the fatigue degree is higher. Alternatively, the detection marker may be lit and flashed according to the risk estimation result. A flashing period may be changed according to the risk estimation result. For example, as indicated by the detection marker 104, when the fatigue degree is relatively low, the detection marker may be displayed by a broken line.

As explained above, in the present embodiment, the risk of deterioration in the endoscopy quality is estimated by the analysis of the fatigue degree of the user and the display form of the detection marker is changed based on the risk estimation result. Consequently, when the fatigue degree of the user is relatively high, it is possible to prevent overlooking of the detection marker and improve the endoscopy quality by, for example, clearly displaying the detection marker. When the fatigue degree of the user is relatively low, it is possible to improve the endoscopy quality by displaying the detection marker not to deteriorate visibility of the observation image.

Third Embodiment

Figure 11:
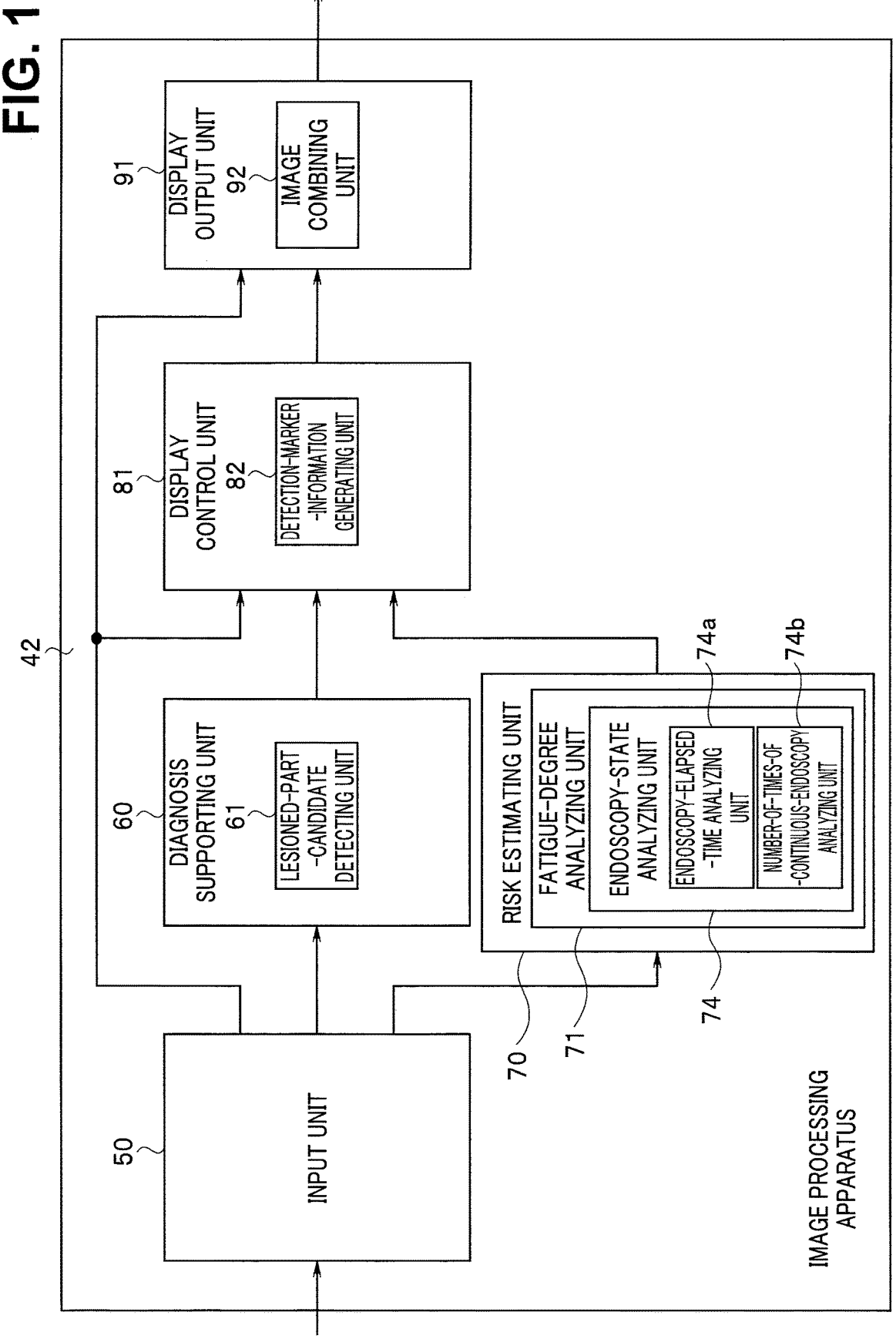
FIG. 11 is a block diagram showing a third embodiment of the present invention.

FIG. 11 is a block diagram showing a third embodiment of the present invention. An endoscope system in the present embodiment is different from the endoscope system 1 shown in FIG. 1 in that an image processing apparatus 42 is adopted instead of the image processing apparatus 40. The image processing apparatus 42 shown in FIG. 11 is different from the image processing apparatus 41 shown in FIG. 4 in that the fatigue-degree analyzing unit 71 is configured by an endoscopy-state analyzing unit 74. The other components are the same as the components in the second embodiment and explanation of the components is omitted. The present embodiment is an example in which a fatigue degree of a user is estimated by an analysis of an endoscopy state.

The endoscopy-state analyzing unit 74 analyzes a state of an endoscopy to analyze the fatigue degree of the user. In the present embodiment, as an example, the endoscopy-state analyzing unit 74 is configured by an endoscopy-elapsed-time analyzing unit 74a and a number-of-times-of-continuous-endoscopy analyzing unit 74b.

The endoscopy-elapsed-time analyzing unit 74a is configured to analyze an endoscopy elapsed time. For example, the endoscopy-elapsed-time analyzing unit 74a calculates a time in which the user performs the endoscopy in any period acquired by the various methods explained above. At the endoscopy time, information for specifying a tester such as a name of the tester is inputted. The endoscopy-elapsed-time analyzing unit 74a is capable of analyzing the endoscopy elapsed time with system information. Note that the information for specifying the tester is sometimes included in an observation image separately from the system information. The endoscopy-elapsed-time analyzing unit 74a is also capable of analyzing endoscopy elapsed times of respective users from the observation image.

For example, as a freely selected time, for example, one day, one week, one month, and the like can be set. For example, when the endoscopy elapsed times in one day are relatively long about the respective users, fatigue degrees are considered to increase as the elapsed times increase. The fatigue-degree analyzing unit 71 can analyze that the fatigue degree is higher as the endoscopy elapsed time calculated by the endoscopy-elapsed-time analyzing unit 74a is longer. The risk estimating unit 70 can estimate that the risk of deterioration in the endoscopy quality increases.

The number-of-times-of-continuous-endoscopy analyzing unit 74b analyzes the numbers of times of continuous endoscopy of the endoscopy about the respective users. The number-of-times-of-continuous-endoscopy analyzing unit 74b is capable of analyzing the number of times of continuous endoscopy for each of the users with the system information. The number-of-times-of-continuous-endoscopy analyzing unit 74b is also capable of analyzing the numbers of times of continuous endoscopy of the respective users from the observation image.

For example, it is assumed that a plurality of times of the endoscopy are performed in one day. The fatigue degree is different between when the same user continuously performs the endoscopy and when a plurality of users perform the endoscopy while taking turns. The fatigue degree is considered to increase as the number of times the same user continuously performs the endoscopy is larger. The fatigue-degree analyzing unit 71 can analyze that the fatigue degree is higher as the number of times of continuous endoscopy calculated by the number-of-times-of-continuous-endoscopy analyzing unit 74b is larger. The risk estimating unit 70 can estimate that the risk of deterioration in the endoscopy quality increases.

Note that, in the present embodiment, the example is explained in which the endoscopy-state analyzing unit 74 is configured by the endoscopy-elapsed-time analyzing unit 74a and the number-of-times-of-continuous-endoscopy analyzing unit 74b. However, the endoscopy-state analyzing unit 74 may be configured by one of the endoscopy-elapsed-time analyzing unit 74a and the number-of-times-of-continuous-endoscopy analyzing unit 74b.

Figure 12:
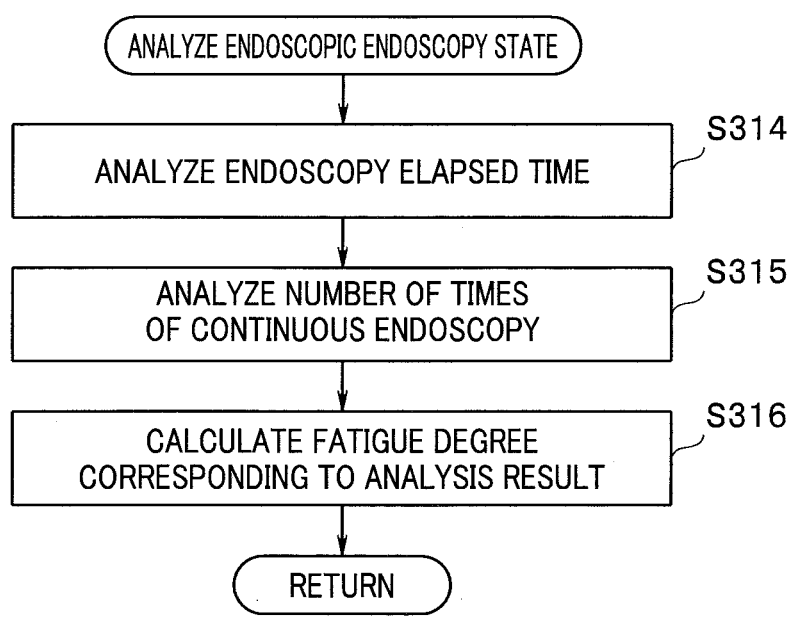
FIG. 12 is a flowchart for explaining operation in the third embodiment.

Subsequently, operation in the embodiment configured as explained above is explained with reference to FIG. 12. FIG. 12 is a flowchart for explaining operation in the third embodiment.

The operation in the present embodiment is the same as the operation shown in FIG. 3 and FIG. 6. FIG. 12 shows an example of a specific flow different from the flow shown in FIG. 7 about step S31 in FIG. 6.

The fatigue-degree analyzing unit 71 of the risk estimating unit 70 analyzes the fatigue degree of the user in step S31 in FIG. 6. For example, the fatigue-degree analyzing unit 71 analyzes, with the endoscopy-state analyzing unit 74, endoscopy states of the respective users. FIG. 12 shows an example of specific processing of the endoscopy-state analyzing unit 74. The endoscopy-state analyzing unit 74 analyzes an endoscopy elapsed time of the endoscopy with the endoscopy-elapsed-time analyzing unit 74a (S314). The endoscopy-state analyzing unit 74 analyzes the number of times of continuous endoscopy of the endoscopy with the number-of-times-of-continuous-endoscopy analyzing unit 74b (S315).

The analyses in steps S314 and S315 may be performed in reverse order or only one of the analyses may be performed. The fatigue-degree analyzing unit 71 calculates a fatigue degree based on an analysis result of at least one of the analyzed endoscopy elapsed time or the analyzed number of times of continuous endoscopy (S316). The fatigue-degree analyzing unit 71 outputs the calculated fatigue degree to the display control unit 81 as a risk estimation result. Note that the fatigue-degree analyzing unit 71 estimates that the fatigue degree is higher and the risk of deterioration in the quality is higher as the endoscopy elapsed time is longer and as the number of times of continuous endoscopy is larger.

As in the second embodiment, the detection-marker-information generating unit 82 of the display control unit 81 generates information for displaying a detection marker in a form corresponding to the risk estimation result. As a result, a detection marker in a form corresponding to the fatigue degree of the user is displayed on the display screen 95a of the display apparatus 95.

The other actions are the same as the actions in the second embodiment. In this way, in the present embodiment, the same effects as the effects in the second embodiment can be obtained.

Fourth Embodiment

Figure 13:
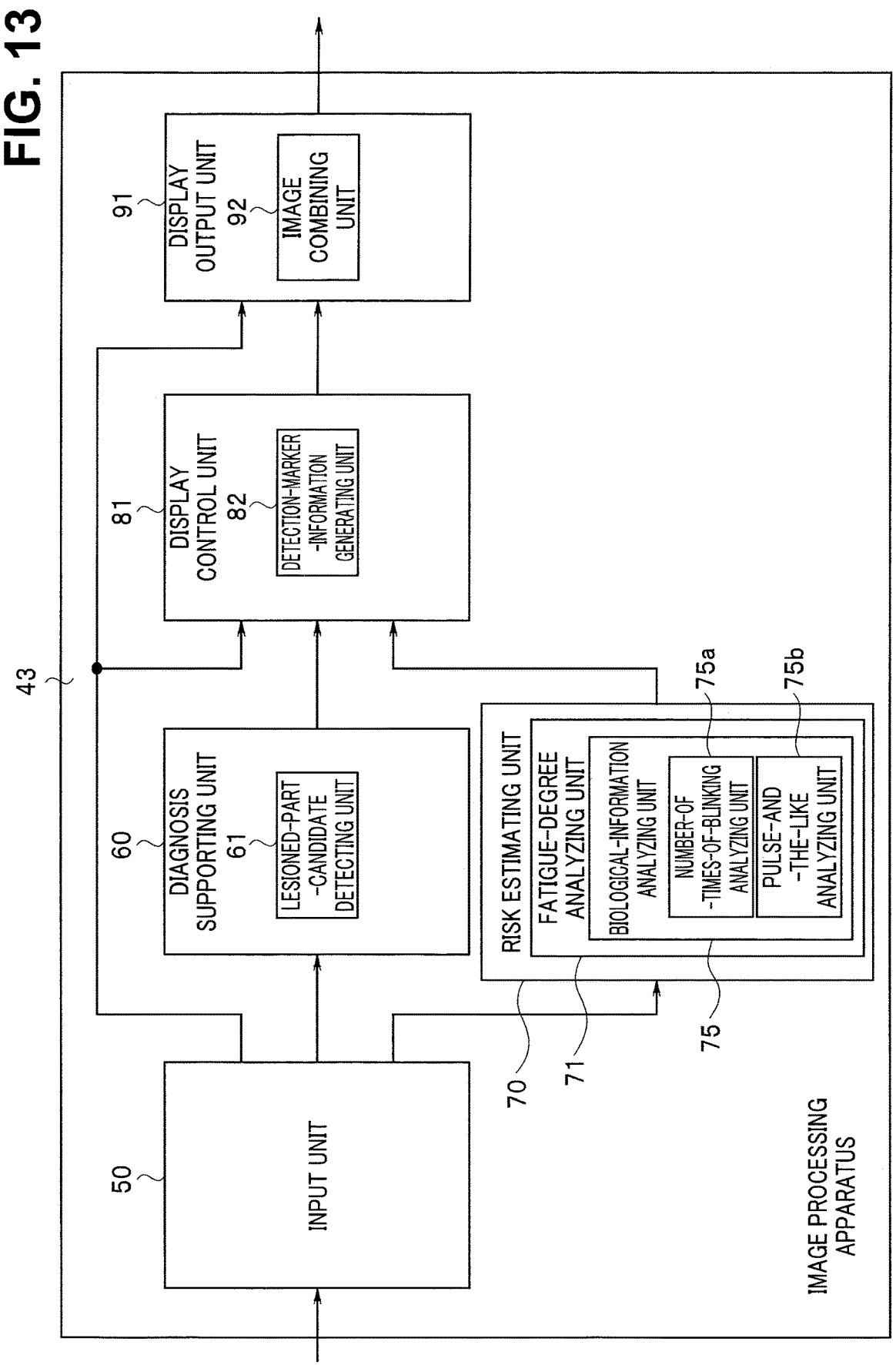
FIG. 13 is a block diagram showing a fourth embodiment of the present invention.

FIG. 13 is a block diagram showing a fourth embodiment of the present invention. An endoscope system in the present embodiment is different from the endoscope system 1 shown in FIG. 1 in that an image processing apparatus 43 is adopted instead of the image processing apparatus 40. The image processing apparatus 43 shown in FIG. 13 is different from the image processing apparatus 41 shown in FIG. 4 in that the fatigue-degree analyzing unit 71 is configured by a biological-information analyzing unit 75. The other components are the same as the components in the second embodiment and explanation of the components is omitted. The present embodiment is an example in which a fatigue degree of a user is estimated by an analysis of biological information.

The biological-information analyzing unit 75 analyzes the biological information to analyze the fatigue degree of the user. In the present embodiment, as an example, the biological-information analyzing unit 75 is configured by a number-of-times-of-blinking analyzing unit 75a and a pulse-and-the-like analyzing unit 75b.

The number-of-times-of-blinking analyzing unit 75a is configured to analyze the number of times of blinking of the user. In an endoscopy room or the like, an operating field camera and the like are provided. Image pickup of a face part of the user with the camera is possible. Images from the cameras are also inputted to the video processor 31. The video processor 31 can calculate, with an image analysis of a picked-up image of the user, the number of times the user blinks. The video processor 31 can output the number of times of blinking of the user to the image processing apparatus 43 as system information. The number-of-times-of-blinking analyzing unit 75a analyzes the number of times of blinking of the user with the inputted system information.

Note that although an example in which information concerning the number of times of blinking is acquired from the image is explained above, the information may be acquired from devices such as various sensors other than the image or may be acquired from the system information.

Note that the risk estimating unit 70 may be configured to capture picked-up images of the user picked up by the operating field camera and the like. In this case, the number-of-times-of-blinking analyzing unit 75a is capable of calculating the number of times of blinking of the user with an image analysis for the captured picked-up images of the user.

The fatigue degree of the user is considered to be larger as the number of times of blinking is larger. The fatigue-degree analyzing unit 71 can analyze that the fatigue degree is higher as the number of times of blinking calculated by the number-of-times-of-blinking analyzing unit 75a is larger. The risk estimating unit 70 can estimate that the risk of deterioration in the endoscopy quality increases.

The pulse-and-the-like analyzing unit 75b analyzes pulses, body temperatures, saturated oxygen amounts, and the like about respective users. The pulse-and-the-like analyzing unit 75b is capable of performing these analyses for each of the users with the system information. The fatigue-degree analyzing unit 71 analyzes the fatigue degree of the users with analysis results of the pulses, the body temperatures, the saturated oxygen amounts, and the like.

Note that, in the present embodiment, the example is explained in which the biological-information analyzing unit 75 is configured by the number-of-times-of-blinking analyzing unit 75a and the pulse-and-the-like analyzing unit 75b. However, the biological-information analyzing unit 75 may be configured by one of the number-of-times-of-blinking analyzing unit 75a and the pulse-and-the-like analyzing unit 75b.

Figure 14:
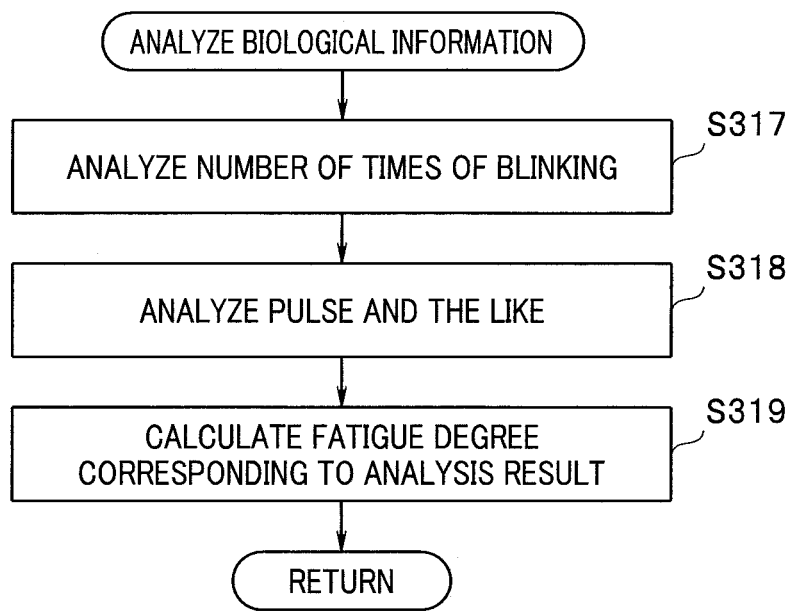
FIG. 14 is a flowchart for explaining operation in the fourth embodiment.

Subsequently, operation in the embodiment configured as explained above is explained with reference to FIG. 14. FIG. 14 is a flowchart for explaining operation in the fourth embodiment.

The operation in the present embodiment is the same as the operation shown in FIG. 3 and FIG. 6. FIG. 14 shows an example of a specific flow different from the flow shown in FIG. 7 about step S31 in FIG. 6.

The fatigue-degree analyzing unit 71 of the risk estimating unit 70 analyzes the fatigue degree of the user in step S31 in FIG. 6. For example, the fatigue-degree analyzing unit 71 analyzes biological information of the respective users with the biological-information analyzing unit 75. FIG. 14 shows an example of specific processing of the biological-information analyzing unit 75. The biological-information analyzing unit 75 analyzes the number of times of blinking with the number-of-times-of-blinking analyzing unit 75a (S317). The endoscopy-state analyzing unit 74 analyzes a pulse, a body temperature, a saturated oxygen amount, and the like of the user with the pulse-and-the-like analyzing unit 75b (S318).

Note that the analyses of steps S317 and S318 may be performed in reverse order or only one of the analyses may be performed. The fatigue-degree analyzing unit 71 calculates a fatigue degree based on an analysis result of at least one of the analyzed number of times of blinking, the analyzed pulse, or the like (S319). The fatigue-degree analyzing unit 71 outputs the calculated fatigue degree to the display control unit 81 as the risk estimation result. Note that the fatigue-degree analyzing unit 71 estimates that the fatigue degree is higher and the risk of deterioration in the endoscopy quality is higher as the number of times of blinking is larger. The fatigue-degree analyzing unit 71 may calculate the fatigue degree based on changes of the pulse, the body temperature, and the saturated oxygen amount of the user during an endoscopy or may store information at normal time of each of the users and calculate the fatigue degree by comparing the pulse, the body temperature, and the saturated oxygen amount of the user during an endoscopy with the stored information.

As in the second embodiment, the detection-marker-information generating unit 82 of the display control unit 81 generates information for displaying a detection marker in a form corresponding to the risk estimation result. As a result, a detection marker in a form corresponding to the fatigue degree of the user is displayed on the display screen 95a of the display apparatus 95.

The other actions are the same as the actions in the second embodiment. In this way, in the present embodiment as well, the same effects as the effects in the second embodiment can be obtained.

Note that, as the risk estimating unit 70, the fatigue-degree analyzing unit 71 including at least one of the number-of-times-of-hold-change analyzing unit 73a, the number-of-times-of-twisting analyzing unit 73b, the endoscopy-elapsed-time analyzing unit 74a, the number-of-times-of-continuous-endoscopy analyzing unit 74b, the number-of-times-of-blinking analyzing unit 75a, or the pulse-and-the-like analyzing unit 75b may be adopted to analyze the fatigue degree of the user.

Fifth Embodiment

Figure 15:
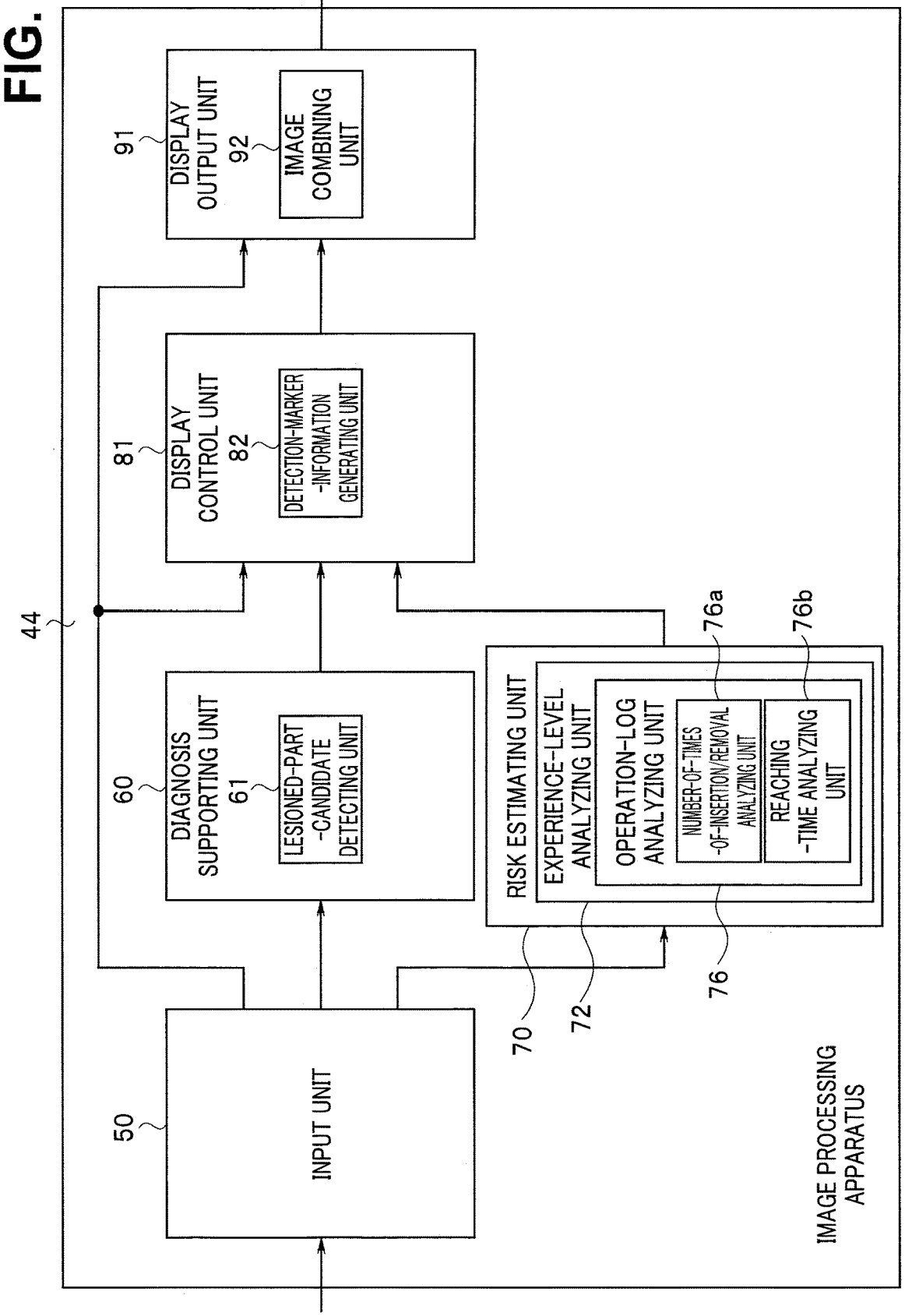
FIG. 15 is a block diagram showing a fifth embodiment of the present invention.

FIG. 15 is a block diagram showing a fifth embodiment of the present invention. An endoscope system in the present embodiment is different from the endoscope system 1 shown in FIG. 1 in that an image processing apparatus 44 is adopted instead of the image processing apparatus 40. FIG. 15 shows an example of a specific configuration of the image processing apparatus 44. The image processing apparatus 44 shown in FIG. 15 is different from the image processing apparatus 41 shown in FIG. 4 in that the risk estimating unit 70 adopts an experience-level analyzing unit 72 instead of the fatigue-degree analyzing unit 71. The other components are the same as the components in the second embodiment and explanation of the components is omitted. The present embodiment is an example in which a risk of deterioration in endoscopy quality is estimated by an analysis of an experience level of a user.

The risk estimating unit 70 includes the experience-level analyzing unit 72. The experience-level analyzing unit 72 analyzes the experience level of the user to obtain an analysis result. The risk estimating unit 70 may use the analysis result of the experience-level analyzing unit 72 as a risk estimation result. In the present embodiment, the experience-level analyzing unit 72 is configured by an operation-log analyzing unit 76. The operation-log analyzing unit 76 analyzes an operation log of the endoscope 21 to analyze the experience level of the user. In the present embodiment, as an example, the operation-log analyzing unit 76 is configured by a number-of-times-of-insertion/removal analyzing unit 76a and a reaching-time analyzing unit 76b.

The number-of-times-of-insertion/removal analyzing unit 76a is configured to analyze the number of times of insertion/removal of the endoscope 21 with the operation log of the endoscope 21. For example, the number-of-times-of-insertion/removal analyzing unit 76a calculates the number of times of insertion/removal of the insertion section 22 from when the insertion section 22 starts to be inserted into a body until when the insertion section 22 reaches an endoscopy target part. According to an act of the user inserting and removing the insertion section 22, the image pickup unit 24 provided in the insertion section 22 also moves and an observation image changes. For example, the number-of-times-of-insertion/removal analyzing unit 76a may be configured to detect such a change of the observation image with an image analysis for the observation image to analyze the insertion and the removal of the insertion section 22 by the user and acquire the number of times of the insertion and the removal. For example, it is also possible to attach a not-shown acceleration sensor or the like to the insertion section 22 in order to analyze the number of times of insertion/removal by analyzing an output of the acceleration sensor. The risk estimating unit 70 may acquire such an output of the acceleration sensor as system information to analyze the number of times of insertion/removal.

The reaching-time analyzing unit 76b is configured to analyze, with the operation log of the endoscope 21, a time period (a reaching time) required for the insertion section 22 to reach the endoscopy target part. In other words, the reaching-time analyzing unit 76b calculates a time period from when the insertion section 22 starts to be inserted into the body until when the insertion section 22 reaches the endoscopy target part. It is possible to detect an insertion start time and an endoscopy target part reaching time of the insertion section 22 with an image analysis of the observation image and clocking by a timer or the like. The reaching-time analyzing unit 76b may be configured to analyze the reaching time with the image analysis of the observation image. For example, it is also possible to transmit the insertion start time and the endoscopy target part reaching time to the video processor 31 with operation of an endoscope switch by the user. The risk estimating unit 70 may acquire these time points as the system information to analyze the reaching time.

The experience-level analyzing unit 72 may analyze the experience level of the user according to at least one of the number of times of insertion/removal calculated by the number-of-times-of-insertion/removal analyzing unit 76a or the reaching time calculated by the reaching-time analyzing unit 76b and set an analysis result as the risk estimation result. For example, the experience-level analyzing unit 72 may determine that proficiency is higher, that is, the experience level is higher as the number of times of insertion/removal of the insertion section 22 by the user is smaller or the reaching time is shorter and estimate that the risk of deterioration in the endoscopy quality is lower. Conversely, the experience-level analyzing unit 72 may determine that the proficiency is lower, that is, the experience level is lower as the number of times of insertion/removal of the insertion section 22 by the user is larger or the reaching time is longer and estimate that the risk of deterioration in the endoscopy quality is higher. The risk estimation result based on the experience level of the user from the risk estimating unit 70 is supplied to the display control unit 81.

Note that, in the present embodiment, the example is explained in which the operation-log analyzing unit 76 is configured by the number-of-times-of-insertion/removal analyzing unit 76a and the reaching-time analyzing unit 76b. However, the operation-log analyzing unit 76 may be configured by one of the number-of-times-of-insertion/removal analyzing unit 76a and the reaching-time analyzing unit 76b.

Figure 16:
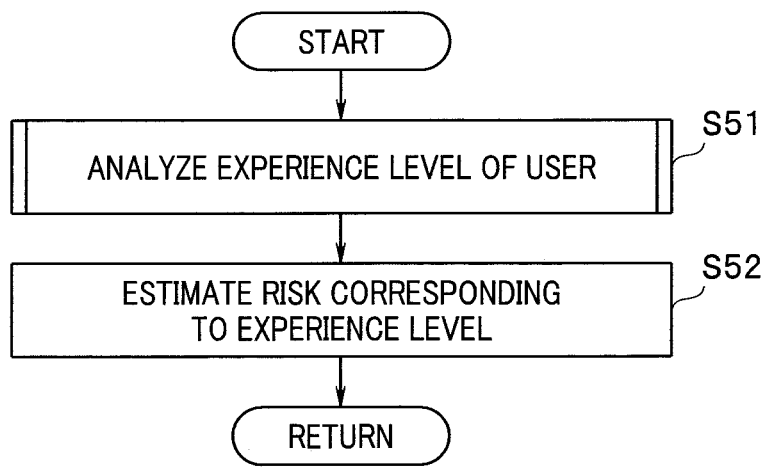
FIG. 16 is a flowchart for explaining operation in the fifth embodiment.
Figure 17:
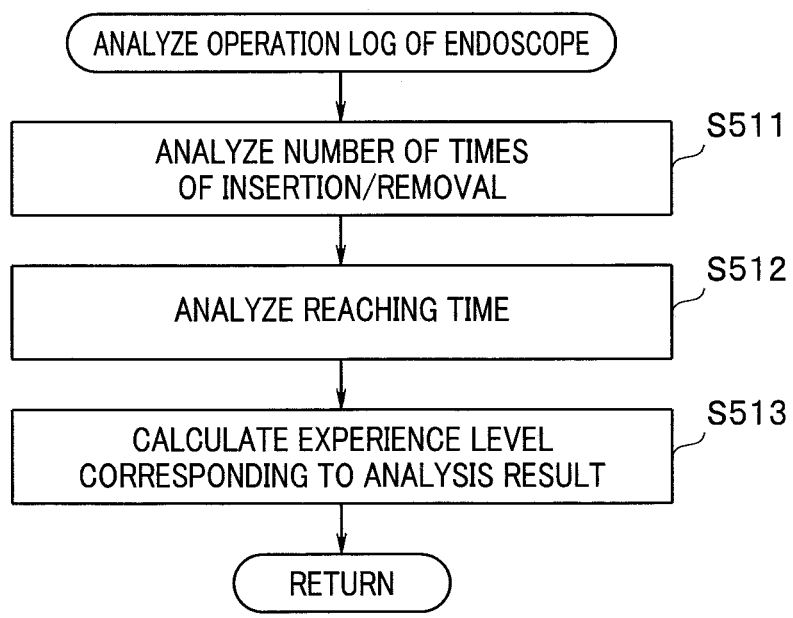
FIG. 17 is a flowchart for explaining the operation in the fifth embodiment.

Subsequently, operation in the embodiment configured as explained above is explained with reference to FIG. 16 and FIG. 17. FIG. 16 and FIG. 17 are flowcharts for explaining operation in the fifth embodiment.

The operation in the present embodiment is the same as the operation shown in FIG. 3. FIG. 16 shows an example of a specific flow about step S3 in FIG. 3. FIG. 17 shows an example of a specific flow of step S51 in FIG. 16.

Acquisition of an observation image, detection of a lesioned part candidate, and display control are the same as the acquisition of an observation image, the detection of a lesioned part candidate and the display control in the second embodiment. The present embodiment is different from the second embodiment in a method of risk estimation.

The experience-level analyzing unit 72 of the risk estimating unit 70 analyzes the experience level of the user in step S51 in FIG. 16. For example, the experience-level analyzing unit 72 analyzes the operation log of the endoscope 21 with the operation-log analyzing unit 76. FIG. 17 shows an example of specific processing of the operation-log analyzing unit 76. The operation-log analyzing unit 76 analyzes the number of times of insertion/removal of the insertion section 22 with the number-of-times-of-insertion/removal analyzing unit 76a (S511). The operation-log analyzing unit 76 analyzes, with the reaching-time analyzing unit 76b, a reaching time until the insertion section 22 reaches the endoscopy target part (S512).

Note that the analysis of the number of times of insertion/removal and the analysis of the reaching time in steps S511 and S512 may be performed in reverse order or only one of the analyses may be performed. The experience-level analyzing unit 72 calculates an experience level of the user based on an analysis result of at least one of the analyzed number of times of insertion/removal or the analyzed reaching time (S513). The experience-level analyzing unit 72 outputs the calculated experience level to the display control unit 81 as the risk estimation result. Note that the experience-level analyzing unit 72 may set numerical values of the number of times of insertion/removal and the reaching time as an analysis result of the experience level and directly output the analysis result of the experience level as the risk estimation result. In this case, it is estimated that the proficiency is lower (the experience level is lower) and the risk of deterioration in the quality is higher as the number of times of insertion/removal is larger and the reaching time is longer.

The detection-marker-information generating unit 82 of the display control unit 81 sets a form of the detection marker based on the inputted risk estimation result and generates, according to the setting, information for displaying the detection marker. For example, the detection-marker-information generating unit 82 sets, with the display-time control unit 83, a display time based on the risk estimation result (S41 in FIG. 8) and sets, with the display-content control unit 84, display content based on the risk estimation result (S42 in FIG. 8).

In this way, the detection marker is displayed in the display form according to the risk estimation result.

For example, when the number of times of insertion/removal is large or the reaching time is long, the detection marker is displayed for a relatively long time in a more conspicuous color tone based on the risk estimation result. Consequently, about a user having a low experience level, it is possible to prevent overlooking of the detection marker and, as a result, achieve improvement of the endoscopy quality.

Conversely, when the number of times of insertion/removal is small or the reaching time is short, the detection marker is displayed for a relatively short time in a more natural color tone based on the risk estimation result. Consequently, about a user having a high experience level, it is possible to prevent visibility of the observation image from being deteriorated by the detection marker and, as a result, achieve improvement of the endoscopy quality.

As explained above, in the present embodiment, the risk of deterioration in the endoscopy quality is estimated by the analysis of the experience level of the user. The display form of the detection marker is changed based on the risk estimation result. Consequently, when the experience level of the user is relatively low, it is possible to prevent overlooking of the detection marker and improve the endoscopy quality by, for example, clearly displaying the detection marker. When the experience level of the user is relatively high, it is possible to improve the endoscopy quality by displaying the detection marker such that the visibility of the observation image is not deteriorated.

Sixth Embodiment

Figure 18:
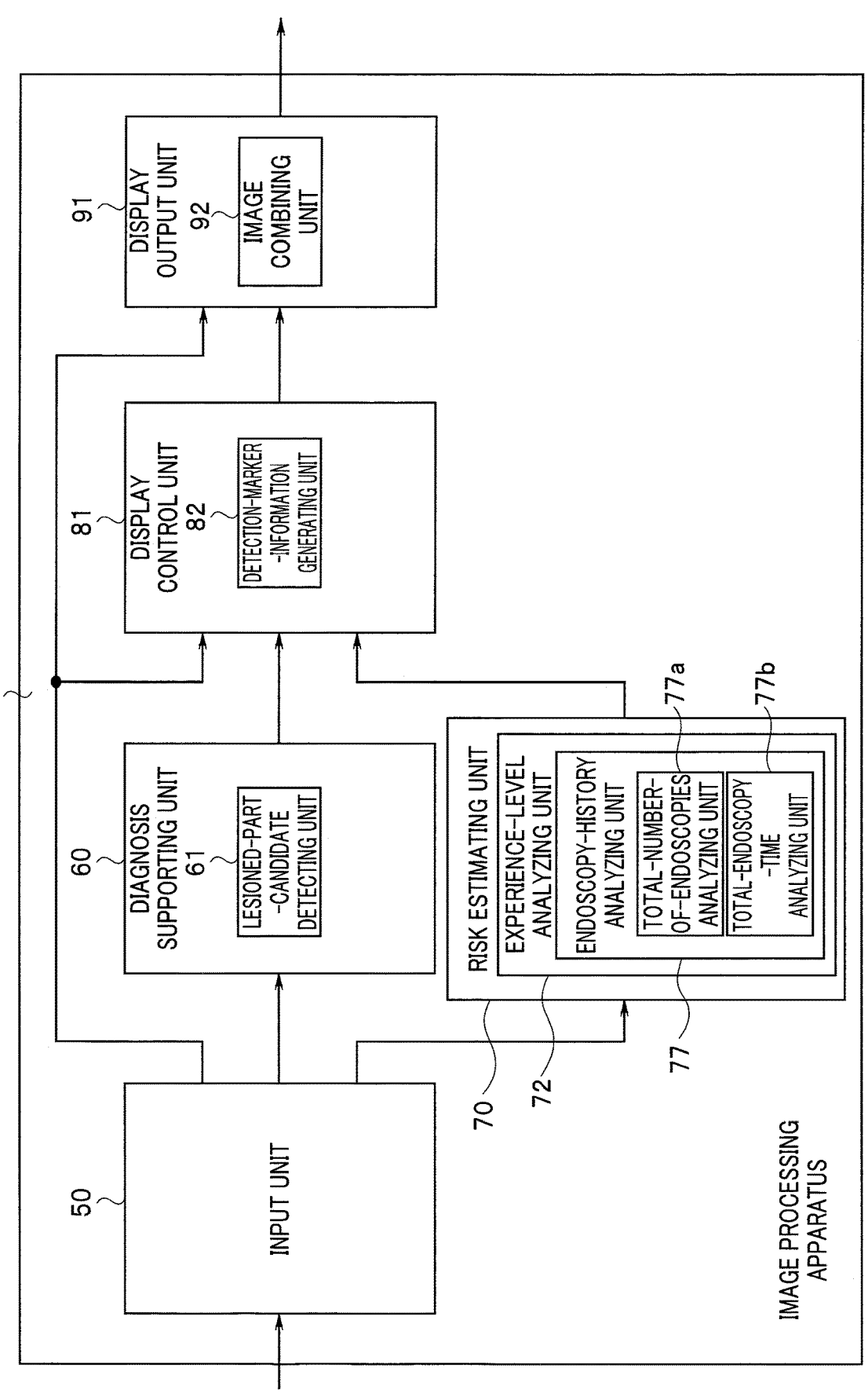
FIG. 18 is a block diagram showing a sixth embodiment of the present invention.

FIG. 18 is a block diagram showing a sixth embodiment of the present invention. An endoscope system in the present embodiment is different from the endoscope system 1 shown in FIG. 1 in that an image processing apparatus 45 is adopted instead of the image processing apparatus 40. The image processing apparatus 45 shown in FIG. 18 is different from the image processing apparatus 44 shown in FIG. 15 in that the experience-level analyzing unit 72 is configured by an endoscopy-history analyzing unit 77. The other components are the same as the components in the fifth embodiment and explanation of the components is omitted. The present embodiment is an example in which an experience level of a user is estimated by an analysis of an endoscopy history.

The endoscopy-history analyzing unit 77 analyzes a history of an endoscopy to analyze the experience level of the user. In the present embodiment, as an example, the endoscopy-history analyzing unit 77 is configured by a total-number-of-endoscopies analyzing unit 77a and a total-endoscopy-time analyzing unit 77b.

The total-number-of-endoscopies analyzing unit 77a is configured to analyze a total number of endoscopies. For example, the total-number-of-endoscopies analyzing unit 77a calculates the number of times the user performs the endoscopy in any period acquired by the various methods explained above. At the endoscopy time, information for specifying a tester such as a name of the tester is inputted. The total-number-of-endoscopies analyzing unit 77a is capable of analyzing the total number of endoscopies with system information. Note that the information for specifying the tester is sometimes included in an observation image separately from the system information. The total-number-of-endoscopies analyzing unit 77a is also capable of analyzing the numbers of endoscopies of respective users from the observation image.

The total-endoscopy-time analyzing unit 77b is configured to analyze a total endoscopy time. For example, the total-endoscopy-time analyzing unit 77b calculates a time period in which the user performs the endoscopy in any period acquired by the various methods explained above. The total-endoscopy-time analyzing unit 77b is capable of analyzing the total endoscopy time with the system information. Note that the total-endoscopy-time analyzing unit 77b is also capable of analyzing total endoscopy times of the respective users from the observation image.

For example, as a freely selected period, for example, one day, one week, and one month can be set. For example, when total numbers of endoscopies in a year are relatively large and the total endoscopy times are relatively long about the respective users, the proficiency (the experience level) is considered to be high. The experience-level analyzing unit 72 can analyze that the experience level is higher as the total number of endoscopies calculated by the total-number-of-endoscopies analyzing unit 77a is larger and the total endoscopy time calculated by the total-endoscopy-time analyzing unit 77b is longer. The risk estimating unit 70 can estimate that the risk of deterioration in the endoscopy quality is small.

Note that, in the present embodiment, the example is explained in which the endoscopy-history analyzing unit 77 is configured by the total-number-of-endoscopies analyzing unit 77*a* and the total-endoscopy-time analyzing unit 77*b*. However, the endoscopy-history analyzing unit 77 may be configured by one of the total-number-of-endoscopies analyzing unit 77*a* and the total-endoscopy-time analyzing unit 77*b*.

Figure 19:
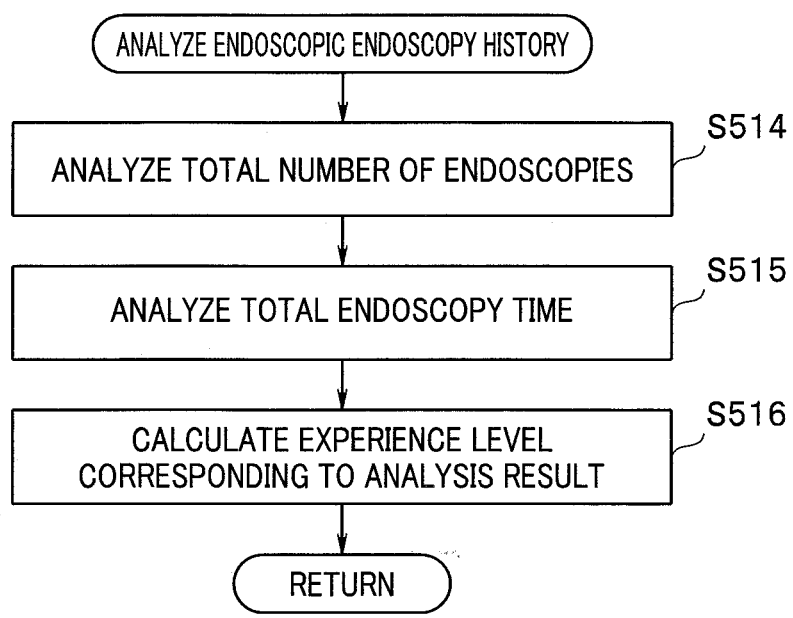
FIG. 19 is a flowchart for explaining operation in the sixth embodiment.

Subsequently, operation in the embodiment configured as explained above is explained with reference to FIG. 19. FIG. 19 is a flowchart for explaining operation in the sixth embodiment.

The operation in the present embodiment is the same as the operation shown in FIG. 3 and FIG. 16. FIG. 19 shows an example of a specific flow different from the flow shown in FIG. 17 about step S51 in FIG. 16.

The experience-level analyzing unit 72 of the risk estimating unit 70 analyzes the experience level of the user in step S51 in FIG. 16. For example, the experience-level analyzing unit 72 analyzes endoscopy histories of respective users with the endoscopy-history analyzing unit 77. FIG. 19 shows an example of specific processing of the endoscopy-history analyzing unit 77. The endoscopy-history analyzing unit 77 analyzes a total number of endoscopies with the total-number-of-endoscopies analyzing unit 77*a* (S514). The endoscopy-history analyzing unit 77 analyzes a total endoscopy time of the endoscopy with the total-endoscopy-time analyzing unit 77*b* (S515).

Note that the analyses in steps S514 and S515 may be performed in reverse order or only one of the analyses may be performed. The experience-level analyzing unit 72 calculates an experience level based on an analysis result of at least one of the analyzed total number of endoscopies or the analyzed total endoscopy time (S516). The experience-level analyzing unit 72 outputs the calculated experience level to the display control unit 81 as a risk estimation result. Note that the experience-level analyzing unit 72 estimates that the experience level is higher and the risk of deterioration in the endoscopy quality is lower as the total number of endoscopies is larger ant the total endoscopy time is longer and estimates that the experience level is lower and the risk of deterioration in the quality is higher as the total number of endoscopies is smaller and the total endoscopy time is shorter.

As in the fifth embodiment, the detection-marker-information generating unit 82 of the display control unit 81 generates information for displaying a detection marker in a form corresponding to the risk estimation result. As a result, a detection marker in a form corresponding to the experience level of the user is displayed on the display screen 95*a* of the display apparatus 95.

The other actions are the same as the actions in the fifth embodiment. In this way, in the present embodiment, the same effects as the effects in the fifth embodiment can be obtained.

Seventh Embodiment

Figure 20:
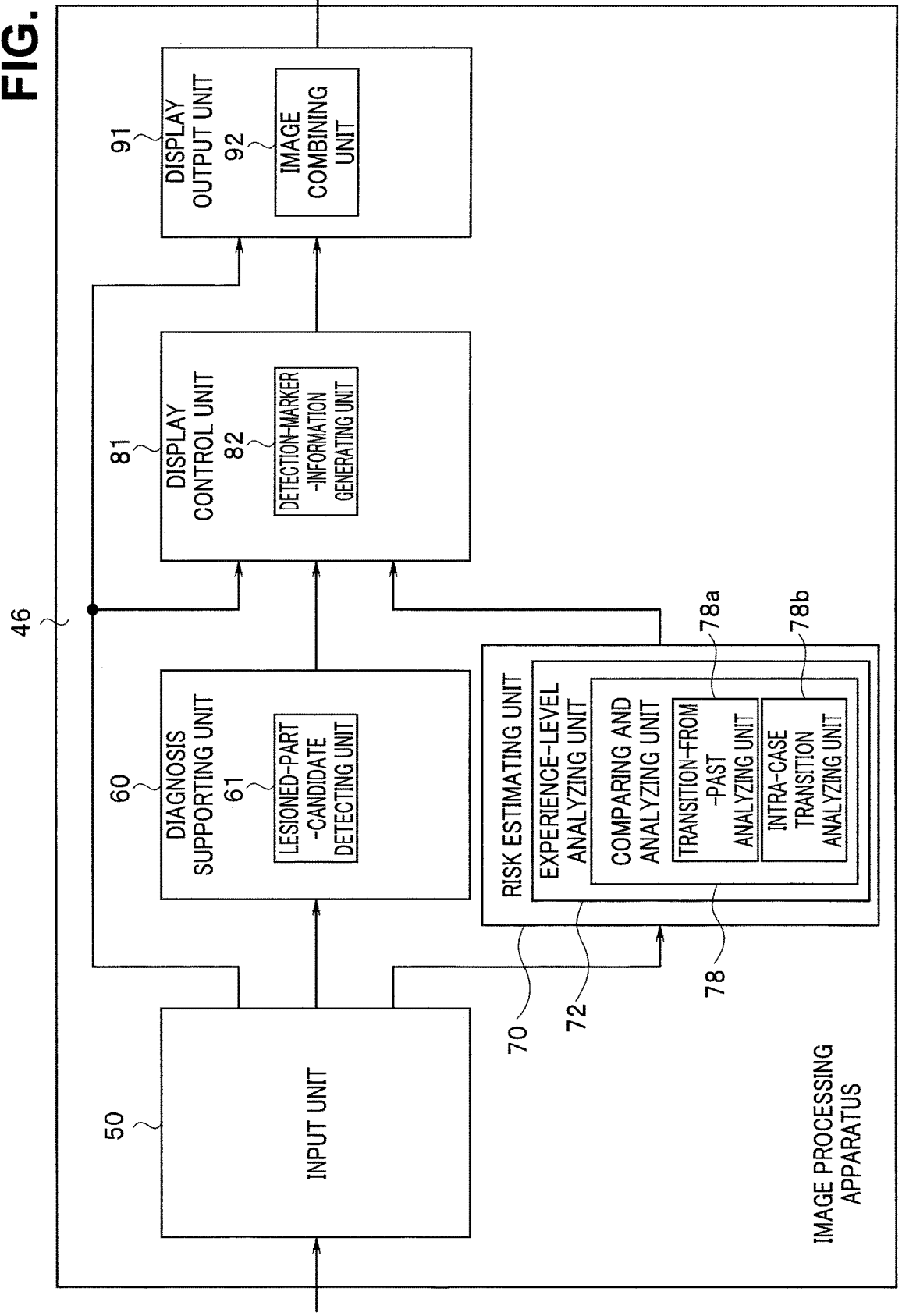
FIG. 20 is a block diagram showing a seventh embodiment of the present invention.

FIG. 20 is a block diagram showing a seventh embodiment of the present invention. An endoscope system in the present embodiment is different from the endoscope system 1 shown in FIG. 1 in that an image processing apparatus 46 is adopted instead of the image processing apparatus 40. The image processing apparatus 46 shown in FIG. 20 is different from the image processing apparatus 44 shown in FIG. 15 in that the experience-level analyzing unit 72 is configured by a comparing and analyzing unit 78. The other components are the same as the components in the fifth embodiment and explanation of the components is omitted. The present embodiment is an example in which an experience level of a user is estimated by an analysis by comparison with a computer aided diagnosis (CAD) apparatus.

The comparing and analyzing unit 78 compares a diagnosis result of the user and a diagnosis result by the CAD for a lesioned part candidate and analyzes transition of a comparison result. In the present embodiment, as an example, the comparing and analyzing unit 78 is configured by a transition-from-past analyzing unit 78*a* and an intra-case transition analyzing unit 78*b*.

The transition-from-past analyzing unit 78*a* compares the diagnosis result of the user and the diagnosis result of the CAD for the lesioned part candidate and analyzes transition indicating how the diagnosis result of the user changes based on the diagnosis result of the CAD. Usually, a degree of correctness of diagnosis for the lesioned part candidate is considered to be in order of an expert doctor having extremely high proficiency≥CAD>an inexperienced doctor. Accordingly, it is considered that a difference between a diagnosis result by the inexperienced doctor and a diagnosis result by the CAD is relatively large and the difference gradually decreases as the doctor accumulates experiences.

Therefore, it is possible to perform comparison of the diagnosis result of the user and the diagnosis result by the CAD, store a comparison result in a not-shown memory, and determine an experience level of the user according to transition of the comparison result. The transition-from-past analyzing unit 78*a* performs recording and readout of such diagnosis results and analyzes the transition of the comparison result. The experience-level analyzing unit 72 determines an experience level of the user based on an analysis result. Note that the risk estimating unit 70 can acquire the diagnosis result of the user and the diagnosis result of the CAD based on the system information.

The intra-case transition analyzing unit 78*b* compares a diagnosis result of the user and a diagnosis result by the CAD for a lesioned part candidate in one case and analyzes transition indicating how the diagnosis result of the user changes based on the diagnosis result of the CAD. At a diagnosis time in one case, when the user accumulates experiences, a difference between the diagnosis result of the user and the diagnosis result by the CAD sometimes decreases. The intra-case transition analyzing unit 78*b* performs recording and readout of diagnosis results in respective cases and analyzes transition of a comparison result. The experience-level analyzing unit 72 determines an experience level of the user based on an analysis result.

Note that, in the present embodiment, the example is explained in which the comparing and analyzing unit 78 is configured by the transition-from-past analyzing unit 78*a* and the intra-case transition analyzing unit 78*b*. However, the comparing and analyzing unit 78 may be configured by one of the transition-from-past analyzing unit 78*a* and the intra-case transition analyzing unit 78*b*.

Figure 21:
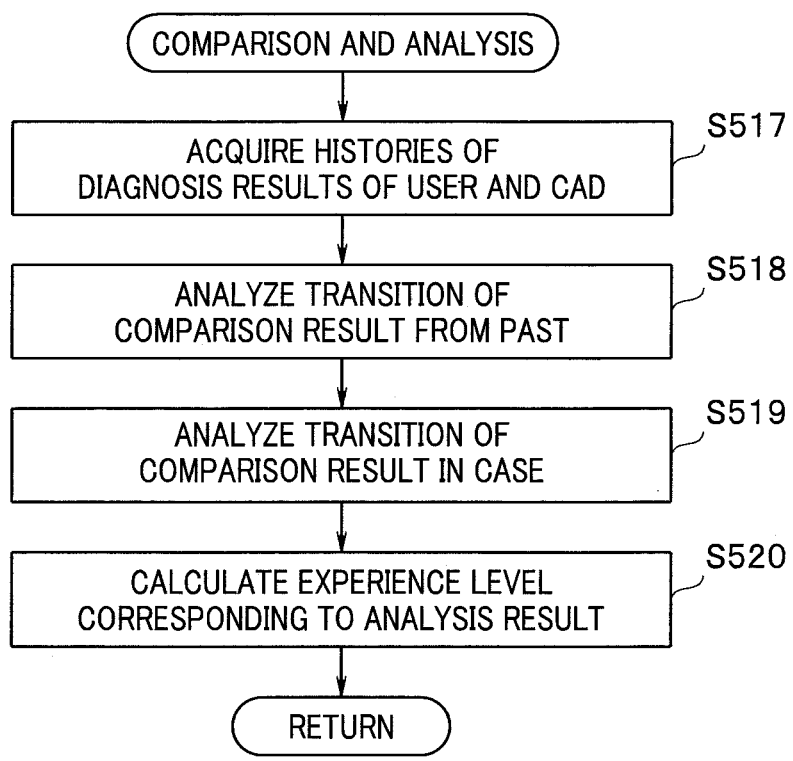
FIG. 21 is a flowchart for explaining operation in the seventh embodiment.

Subsequently, operation in the embodiment configured as explained above is explained with reference to FIG. 21. FIG. 21 is a flowchart for explaining operation in the seventh embodiment.

The operation in the present embodiment is the same as the operation shown in FIG. 3 and FIG. 16. FIG. 21 shows an example of a specific flow different from FIG. 17 about step S5*l* in FIG. 16.

The experience-level analyzing unit 72 of the risk estimating unit 70 analyzes an experience level of the user in step S51 in FIG. 16. The experience-level analyzing unit 72 analyzes the experience level with the comparing and analyzing unit 78. FIG. 21 shows an example of specific processing of the comparing and analyzing unit 78. The comparing and analyzing unit 78 acquires diagnosis results of respective users and a diagnosis result of the CAD (S517 in FIG. 21) and analyzes transition of a difference between a diagnosis result of a user and the diagnosis result of the CAD with the transition-from-past analyzing unit 78*a* (S518). The experience-level analyzing unit 72 analyzes transition of the difference between the diagnosis result of the user and the diagnosis result of the CAD about one case with the intra-case transition analyzing unit 78*b* (S519).

Note that the analyses in steps S518 and S519 may be performed in reverse order or only one of the analyses may be performed. The experience-level analyzing unit 72 calculates an experience level based on at least one analysis result of the analysis result of the analyzed transition from the past and the analysis result of the analyzed transition in one case (S520). For example, the experience-level analyzing unit 72 determines a degree of correctness of the diagnosis result of the user and calculates an experience level of the user according to the transition of the difference between the diagnosis result of the user and the diagnosis result of the CAD. For example, when the difference between the diagnosis result of the user and the diagnosis result of the CAD decreases, it can be determined that the experience level of the user increases.

The risk estimating unit 70 outputs the calculated experience level to the display control unit 81 as a risk estimation result. As in the fifth embodiment, the detection-marker-information generating unit 82 of the display control unit 81 generates information for displaying a detection marker in a form corresponding to the risk estimation result. As a result, a detection marker in a form corresponding to the experience level of the user is displayed on the display screen 95*a* of the display apparatus 95.

The other actions are the same as the actions in the fifth embodiment. In this way, in the present embodiment, the same effects as the effects in the firth embodiment can be obtained.

Note that, as the risk estimating unit 70, the experience-level analyzing unit 72 including at least one of the number-of-times-of-insertion/removal analyzing unit 76*a*, the reaching-time analyzing unit 76*b*, the total-number-of-endoscopies analyzing unit 77*a*, the total-endoscopy-time analyzing unit 77*b*, the transition-from-past analyzing unit 78*a*, or the intra-case transition analyzing unit 78*b* may be adopted to analyze the experience level of the user.

Further, the risk estimating unit 70 may include at least one of the fatigue-degree analyzing unit 71 or the experience-level analyzing unit 72 in the second to seventh embodiments.

In the respective embodiments, when the notification is performed by sound or the like, it is also possible to set a notification form corresponding to the risk estimation result.

Note that, among the techniques explained in the specification, the control mainly explained in the flowcharts can often be set by a program and is sometimes stored in a recording medium or a recording unit. As a method of recording in the recording medium or the recording unit, the control may be recorded at a product shipment time, may be recorded using a distributed recording medium, or may be downloaded via the Internet.

The execution order of the steps in the flowcharts may be changed, a plurality of the steps may be simultaneously executed, or the steps may be executed in different order in every execution unless contrary to natures of the steps.

Note that, in the embodiments, the portion described as "unit" may be configured by a dedicated circuit or may be configured by combining a plurality of general-purpose circuits or may be configured by combining, according to necessity, processors such as a microcomputer and a CPU that perform operation according to software programmed in advance or sequencers such as an FPGA.

The present invention is not limited to the respective embodiments per se. In an implementation stage, the constituent elements can be modified and embodied in a range not departing from the gist of the present invention. Various inventions can be formed by appropriate combinations of a plurality of constituent elements disclosed in the respective embodiments. For example, several constituent elements among all the constituent elements explained in the embodiments may be deleted. Further, the constituent elements in different embodiments may be combined as appropriate.

What is claimed is:

1. An image processing apparatus comprising:
a processor comprising hardware, wherein the processor is configured to:
receive an observation image of a subject or the observation image and system information of an endoscope that captured the observation image;
perform image processing to detect a lesioned part candidate from the observation image;
analyze a fatigue degree of a user operating the endoscope;
estimate a deterioration risk of endoscopy quality based on the fatigue degree;
when detecting the lesioned part candidate, control a notification form of a detection marker for a notification of the lesioned part candidate based on the deterioration risk of the endoscopy quality estimated so that, when the fatigue degree is higher, one or more of:
a display time of the detection marker is set longer;
brightness and chroma of the detection marker is set higher;
thickness of a line of a frame of the detection marker is increased; and
a flashing period of the detection marker is different, compared with when the fatigue degree is relatively low; and
control a display to display the detection marker according to the control of the notification form to perform notification of the lesioned part candidate.

2. The image processing apparatus according to claim 1, wherein the processor is configured to:
analyze an operation log of the endoscope that captured the observation image; and
calculate the fatigue degree based on a result of the analysis of the operation log.

3. The image processing apparatus according to claim 2, wherein the processor is configured to:
analyze the operation log to calculate a number of times of hold change of the endoscope that captured the observation image in a predetermined period; and
calculate the fatigue degree based on the number of times of hold change calculated.

4. The image processing apparatus according to claim 2, wherein the processor is configured to:
analyze the operation log to calculate a number of times of twisting of the endoscope that captured the observation image in a predetermined period; and
calculate the fatigue degree based on the number of times of twisting calculated.

5. The image processing apparatus according to claim 1, wherein the processor is configured to:
   analyze an endoscopy state log of the endoscope that captured the observation image; and
   calculate the fatigue degree based on an endoscopy state obtained as a result of the analysis of the endoscopy state log.

6. The image processing apparatus according to claim 5, wherein the processor is configured to:
   analyze the endoscopy state log to calculate an endoscopy elapsed time in a predetermined period; and
   calculate the fatigue degree based on the endoscopy elapsed time calculated.

7. The image processing apparatus according to claim 5, wherein the processor is configured to:
   analyze the endoscopy state log to calculate a number of times of continuous endoscopy; and
   calculate the fatigue degree based on the number of times of continuous endoscopy calculated.

8. The image processing apparatus according to claim 1, wherein the processor is configured to:
   analyze biological information, captured by one or more sensors, of the user operating the endoscope that captured the observation image; and
   calculate the fatigue degree based on a result of the analysis of the biological information.

9. The image processing apparatus according to claim 8, wherein the processor is configured to:
   analyze the biological information to calculate a number of times of blinking of the user; and
   calculate the fatigue degree based on the number of times of blinking calculated.

10. The image processing apparatus according to claim 1, wherein the processor is configured to:
    analyze an experience level of the user operating the endoscope that captured the observation image; and
    estimate the deterioration risk of the endoscopy quality based on a result of the analysis of the experience level.

11. The image processing apparatus according to claim 10, wherein the processor is configured to:
    analyze an operation log of the endoscope that captured the observation image; and
    calculate the experience level based on a result of the analysis of the operation log.

12. The image processing apparatus according to claim 11, wherein the processor is configured to:
    analyze the operation log to calculate a number of times of insertion/removal of the endoscope that captured the observation image to an endoscopy target part of the endoscope; and
    calculate the experience level based on the number of times of insertion/removal calculated.

13. The image processing apparatus according to claim 11, wherein the processor is configured to:
    analyze the operation log to calculate a reaching time to an endoscopy target part by the endoscope; and
    calculate the experience level based on the reaching time calculated.

14. The image processing apparatus according to claim 10, wherein the processor is configured to:
    analyze, based on an operation log, an endoscopy history of the user; and
    calculate the experience level based on the endoscopy history analyzed.

15. The image processing apparatus according to claim 14, wherein the processor is configured to:
    analyze the operation log to calculate at least one of a total number of endoscopies or a total endoscopy time of an endoscopy in a predetermined period; and
    calculate the experience level based on the at least one of the total number of endoscopies or the total endoscopy time of the endoscopy in the predetermined period.

16. The image processing apparatus according to claim 10, wherein the processor is configured to:
    analyze an operation log to obtain transition of a comparison result of a diagnosis result of the user and a diagnosis result of a computer aided diagnosis apparatus; and
    calculate the experience level based on transition of the comparison result obtained.

17. The image processing apparatus according to claim 16, wherein the processor is configured to calculate the experience level based on at least one of transition of a comparison result from past to present and transition of a comparison result in one endoscopy.

18. The image processing apparatus according to claim 1, wherein the processor is configured to:
    analyze a nature of the lesioned part candidate; and
    change a display determination level of display and non-display of the lesioned part candidate based on the nature of the lesioned part candidate and the deterioration risk of the endoscopy quality estimated.

19. The image processing apparatus according to claim 1, wherein the processor is configured to control the display to display the observation image and the detection marker indicating the lesioned part candidate.

20. A non-transitory computer-readable recording medium recording an image processing program, the image processing program, when executed, causes a computer to at least execute:
    receiving an observation image of a subject or the observation image and system information of an endoscope that captured the observation image;
    performing image processing to detect a lesioned part candidate from the observation image;
    analyzing a fatigue degree of a user operating the endoscope;
    estimating a deterioration risk of endoscopy quality based on the fatigue degree;
    when detecting the lesioned part candidate, controlling a notification form of a detection marker for a notification of the lesioned part candidate based on the deterioration risk of the endoscopy quality estimated so that, when the fatigue degree is higher, one or more of:
    a display time of the detection marker is set longer;
    brightness and chroma of the detection marker is set higher;
    thickness of a line of a frame of the detection marker is increased; and
    a flashing period of the detection marker is different, compared with when the fatigue degree is relatively low; and
    controlling a display to display the detection marker according to the control of the notification form to perform notification of the lesioned part candidate.

21. A diagnosis supporting method comprising:
receiving an observation image of a subject or the observation image and system information of an endoscope that captured the observation image;
performing image processing to detect a lesioned part candidate from the observation image; analyzing a fatigue degree of a user operating the endoscope;
estimating a deterioration risk of endoscopy quality based on the fatigue degree;
when detecting the lesioned part candidate, controlling a notification form of a detection marker for a notification of the lesioned part candidate based on the deterioration risk of the endoscopy quality estimated so that, when the fatigue degree is higher, one or more of:
a display time of the detection marker is set longer;
brightness and chroma of the detection marker is set higher;
thickness of a line of a frame of the detection marker is increased; and
a flashing period of the detection marker is different, compared with when the fatigue degree is relatively low; and
controlling a display to display the detection marker according to the control of the notification form to perform notification of the lesioned part candidate.

* * * * *